United States Patent [19]

Shibuya et al.

[11] Patent Number: 5,789,392
[45] Date of Patent: Aug. 4, 1998

[54] SACCHARIDE COMPOSITION WITH REDUCED REDUCIBILITY, AND PREPARATION AND USES THEREOF

[75] Inventors: Takashi Shibuya; Toshiyuki Sugimoto; Toshio Miyake, all of Okayama, Japan

[73] Assignee: Kabushiki Kaisha Hayashibara Seibutsu Kagaku Kenkyujo, Okayama, Japan

[21] Appl. No.: 883,079

[22] Filed: Jun. 26, 1997

Related U.S. Application Data

[62] Division of Ser. No. 492,691, Jun. 20, 1995, Pat. No. 5,681,826.

[30] Foreign Application Priority Data

Jun. 27, 1994 [JP] Japan .................................. 6-180393

[51] Int. Cl.⁶ .............................. A61K 31/715; C07H 1/00
[52] U.S. Cl. .......................... 514/54; 536/123.1; 536/124
[58] Field of Search .......................... 514/54; 536/123.1, 536/124

[56] References Cited

U.S. PATENT DOCUMENTS

| 4,521,252 | 6/1985 | Miyake et al. ........... 127/46.3 |
| 4,767,625 | 8/1988 | Mitsuno et al. ........... 424/95 |

FOREIGN PATENT DOCUMENTS

| 0447125 | 3/1991 | European Pat. Off. . |
| 0 532 807 A1 | 11/1991 | European Pat. Off. . |
| 0 606 753 A2 | 12/1993 | European Pat. Off. . |
| 50-154485 | 12/1975 | Japan . |
| 58-023799 | 2/1983 | Japan . |
| 58-072598 | 4/1983 | Japan . |
| 58-216695 | 12/1983 | Japan . |
| 281795 | 10/1992 | Japan . |
| 2106912 | 8/1981 | United Kingdom . |
| WO 92/03565 | 3/1992 | WIPO . |

OTHER PUBLICATIONS

Patent Abstracts of Japan (unexamined applications). C filed, vol. 13, No. 3, Jan. 6, 1989. Abstract No. 63–216492 published Aug. 9, 1988.

Pharmaceutical Research, vol. 9, No. 1, issued 1992, Hora et al; "Lyophilized Formulations of Recombinant Tumor Necrosis Factor", pp. 33–36.

Kobayashi, S.; Current Status of Starch Application Development and Related Problems; Food Chemicals; vol. 88, pp. 67–72; Aug. 1992.

Atsuji, H. et al; "Rhinsho–Eiyo"; Journal of Clinical Nutrition; vol. 41, No. 2; pp. 200–208; 1972.

Birch, Gordon A.; "Trehaloses"; Advances in Carbohydrate Chemistry; vol. 18; pp. 201–225; 1963.

Hoelzle, Inger and John G. Streeter; "Increased Accumulation of Trehalose in Rhizobia Cultured Under 1% Oxygen"; Applied Environmental Biology; vol. 56, No. 10; pp. 3213–3215; Oct. 1990.

Primary Examiner—John Kight
Assistant Examiner—Everett White
Attorney, Agent, or Firm—Browdy and Neimark

[57] ABSTRACT

A saccharide composition with a reduced reducibility which is prepared by hydrogenating a saccharide mixture comprising reducing saccharides and non-reducing saccharides consisting of trehalose and/or saccharides having a trehalose structure. The saccharide composition has a satisfactory sweetness, taste and stability, and is substantially free from reducibility, so that it can be freely used in a variety of compositions such as foods, cosmetics and pharmaceuticals which are susceptible to reduction.

9 Claims, 17 Drawing Sheets

SACCHARIDE COMPOSITION WITH REDUCED REDUCIBILITY, AND PREPARATION AND USES THEREOF

This is a divisional of parent application Ser. No. 08/492,961, filed Jun. 20, 1995, now abandoned U.S. Pat. No. 5,681,826.

BACKGROUND OF THE INVENTION

1. Field of the Invention

The present invention relates to a saccharide composition with a reduced reducibility, and preparation and uses thereof, more particularly, to a saccharide composition with a educed reducibility which comprises a sugar alcohol and a non-reducing saccharide consisting of trehalose and/or a saccharide having a trehalose structure.

2. Description of the Prior Art

Trehalose or α,α-trehalose, a non-reducing saccharide consisting of two glucopyranoside residues, has been well known. As is described in Advances in *Carbohydrate Chemistry*, Vol.18, pp.201–225 (1963), published by Academic Press, USA, and Applied and *Environmental Microbiology*, Vol.56, pp.3,213–3,215 (1990), trehalose is widely distributed in microorganisms, mushrooms, insects, etc., though the content is relatively low. Since non-reducing saccharides including trehalose do not react with substances containing amino groups such as amino acids and proteins, they neither induce the amino-carbonyl reaction nor alter amino acid-containing substances. Thus, such non-reducing saccharides have been expected to be used without fear of causing unsatisfiable browning and deterioration, and the preparation of which has been in great demand.

Examples of conventional preparations of trehalose include a method as disclosed in Japanese Patent Laid-Open No.154,485/75 wherein microorganisms are utilized, and a conversion method as proposed in Japanese Patent Laid-Open No.216,695/83 wherein maltose is converted into trehalose by the combination use of maltose- and trehalose-phosphorylases. The former is, however, not suitable for the industrial-scale preparation of trehalose because the content of trehalose present in microorganisms as a starting material is usually lower than 15 w/w % (the wording "w/w %" will be abbreviated as "%" in the present specification, unless specified otherwise), on a dry solid basis (d.s.b.), and the extraction and purification steps are complicated. The latter has the following demerits: (i) Since trehalose is formed via glucose-1-phosphate, the concentration of maltose as a substrate could not be set to a relatively-high concentration; (ii) Since the enzymatic reaction systems of the phosphorylases are reversible reactions, the yield of the objective trehalose is relatively low; and (iii) It is substantially difficult to retain the reaction systems stably and to continue their enzymatic reactions smoothly. Therefore, they have not been established as an industrial-scale preparation.

As regards the preparation of trehalose, it is reported in the column titled "*Oligosaccharides*" in the chapter titled "Current Status of Starch Application Development and Related Problems" in "*Food Chemicals*", No.88, pp.67–72 (August, 1992) that "In spite of a wide applicability of trehalose, an enzymatic preparation thereof via a direct saccharide-transfer reaction or a hydrolytic reaction has been recognized to be scientifically almost impossible," so that an enzymatic preparation of trehalose from starch as a material has been recognized to be scientifically difficult.

It is known that partial starch hydrolysates prepared from starch as a material such as liquefied starch, cyclodextrins and maltooligosaccharides usually have a reducing end-group as an end unit. These partial starch hydrolysates are referred to as "reducing partial starch hydrolysates" in the present specification. The reducing power of such reducing partial starch hydrolysates is generally expressed by "dextrose equivalent (DE) value", based on their dry solid weights. It is known that among reducing partial starch hydrolysates those with a relatively-high DE value generally have a relatively-low molecular weight and viscosity and a relatively-high sweetness and reactivity, and readily react with amino group-containing substances such as amino acids and proteins to induce the amino carbonyl reaction, to cause unsatisfactory browning and smell, and to deteriorate their quality.

These unfavorable properties of such reducing partial starch hydrolysates are varied depending on their DE values, and the relationship between reducing partial starch hydrolysates and their DE values is significantly important. It has been even believed that it is impossible to break away the relationship in this field.

To overcome such conventional drawbacks, the present inventors had disclosed in Japanese Patent Application No.349,216/93 a novel non-reducing saccharide-forming enzyme which forms non-reducing saccharides having a trehalose structure as an end unit from one or more reducing partial starch hydrolysates with a glucose polymerization degree of 3 or more (throughout the present specification, the enzyme is designated as "non-reducing saccharide-forming enzyme"). By using the non-reducing saccharide-forming enzyme, they established the preparation of non-reducing saccharides, which have a glucose polymerization degree of 3 or more and a trehalose structure as an end unit, from reducing partial starch hydrolysates, as well as establishing saccharide compositions with a reduced reducibility and the preparation of trehalose from these non-reducing saccharides and saccharide compositions.

The present inventors also disclosed in Japanese Patent Application No.79,291/94 a novel trehalose-releasing enzyme which specifically hydrolyses the linkage between a trehalose moiety and others in non-reducing saccharides having a glucose polymerization degree of 3 or more and a trehalose structure as an end unit (throughout the present specification, the enzyme is designated as "trehalose-releasing enzyme"), and established the preparation of trehalose in a relatively-high yield from reducing partial starch hydrolysates by the combination use of the aforesaid non-reducing saccharide-forming enzyme and trehalose-releasing enzyme. It was revealed that in the preparations of saccharide compositions having a trehalose structure and a glucose polymerization degree of 3 or more and those of non-reducing saccharides such as trehalose, intact reducing partial starch hydrolysates still remain in the final products, and reducing amylaceous saccharides such as glucose and maltose are newly formed. Required is to more reduce the reducibility of these saccharide compositions with a reduced reducibility which contain the aforesaid non-reducing saccharides and reducing saccharides.

SUMMARY OF THE INVENTION

The present invention is to provide saccharides having a trehalose structure or non-reducing saccharides having a trehalose structure as an end unit (hereinafter designated as "α-glycosyltrehalose" in the present specification), non-reducing saccharides wherein one or more glucose residues bind to the two glucopyranoside residues of trehalose (hereinafter designated as "α-glycosyl α-glycoside" in the present specification), and saccharides prepared by more reducing the reducibility of those with a relatively-low reducibility which contain reducing saccharides and non-reducing saccharides such as trehalose. The present invention is to also provide the preparation and uses of these saccharides.

To overcome those objects, the present inventors energetically studied on the hydrogenation method for the aforesaid saccharides with a low reducibility.

As a result, they found that reducing amylaceous saccharides can be readily converted into their corresponding sugar alcohols by hydrogenating saccharide compositions with a reduced reducibility comprising the reducing amylaceous saccharides and other non-reducing saccharides consisting of trehalose and/or saccharides having a trehalose structure without fear of the affection of the non-reducing saccharides, and that the reducibility of the saccharide compositions as a material is lowered or even substantially diminished.

The present inventors studied on the preparation of the materials usable in the present invention, i.e. saccharide compositions with a relatively-low reducibility which comprise reducing saccharides and non-reducing saccharides consisting of trehalose and/or saccharides having a trehalose structure, and have found that compositions which are obtainable by allowing a non-reducing saccharide-forming enzyme together with or without a trehalose-releasing enzyme to act on reducing partial starch hydrolysates with a glucose polymerization degree of 3 or more can be arbitrarily used. More particularly, saccharide compositions with a low reducibility, which are obtainable by allowing starch debranching enzyme and/or cyclomaltodextrin glucanotransferase to act on liquefied starch solutions when a non-reducing saccharide-forming enzyme is allowed to act on the solutions together with or without a trehalose-releasing enzyme, are satisfactorily used. Furthermore, the present inventors found that saccharide compositions with a low reducibility, which are obtainable by allowing a maltose-trehalose converting enzyme to act on amylaceous substances, as disclosed in Japanese Patent Application No.144,092/94, titled "Maltose-trehalose converting enzyme, and preparation and uses thereof", applied for by the present applicant on the day of Jun. 3, 1994, can be arbitrarily used in the present invention. Thus, they accomplished this invention and revealed that, in the process for preparing such saccharide compositions with a reduced reducibility wherein a non-reducing saccharide-forming enzyme is allowed to act on amylaceous solutions with a DE less than 15, saccharide compositions with a low reducibility, which contain non-reducing saccharides obtainable by allowing a starch debranching enzyme and/or cyclomaltodextrin glucanotransferase to act on the amylaceous solutions, can be suitably used as a material saccharide in the present invention because they have an extremely reduced molecular weight and viscosity and a satisfactory handleability without substantial increment of their initial reducibility than those prepared by the sole use of the non-reducing saccharide-forming enzyme. They also found that the trehalose content in the saccharide compositions with a relatively-low reducibility increases when glucoamylase acts on them. In addition, they found that, in the process for preparing trehalose by allowing a non-reducing saccharide-forming enzyme and a trehalose-releasing enzyme to act on liquefied starch solutions with a relatively-low DE, preferably, those with a DE less than 15, trehalose which is obtainable by using a starch debranching enzyme and/or cyclomaltodextrin glucanotransferase can be suitably used as a material in the present invention because such trehalose is obtained in a relatively-high yield as compared with that obtained by the sole use of the non-reducing saccharide-forming enzyme. Furthermore, it was found that saccharide compositions of trehalose and maltose, which are obtainable by allowing a maltose-trehalose converting enzyme to act on maltose, can be arbitrarily used in the present invention. The resultant saccharide compositions with a low reducibility and rich in non-reducing saccharides consisting of trehalose and/or saccharides having a trehalose structure can be readily hydrogenated. These saccharide compositions are substantially free of reducibility or they have a dextrose equivalent (DE) value less than 1, and have a satisfactory stability, handleability and wide applicability. Thus, they can be arbitrarily used in a variety of compositions such as foods, cosmetics and pharmaceuticals.

BRIEF DESCRIPTION OF THE ACCOMPANYING DRAWINGS

DETAILED DESCRIPTION OF THE INVENTION

Figure 1:
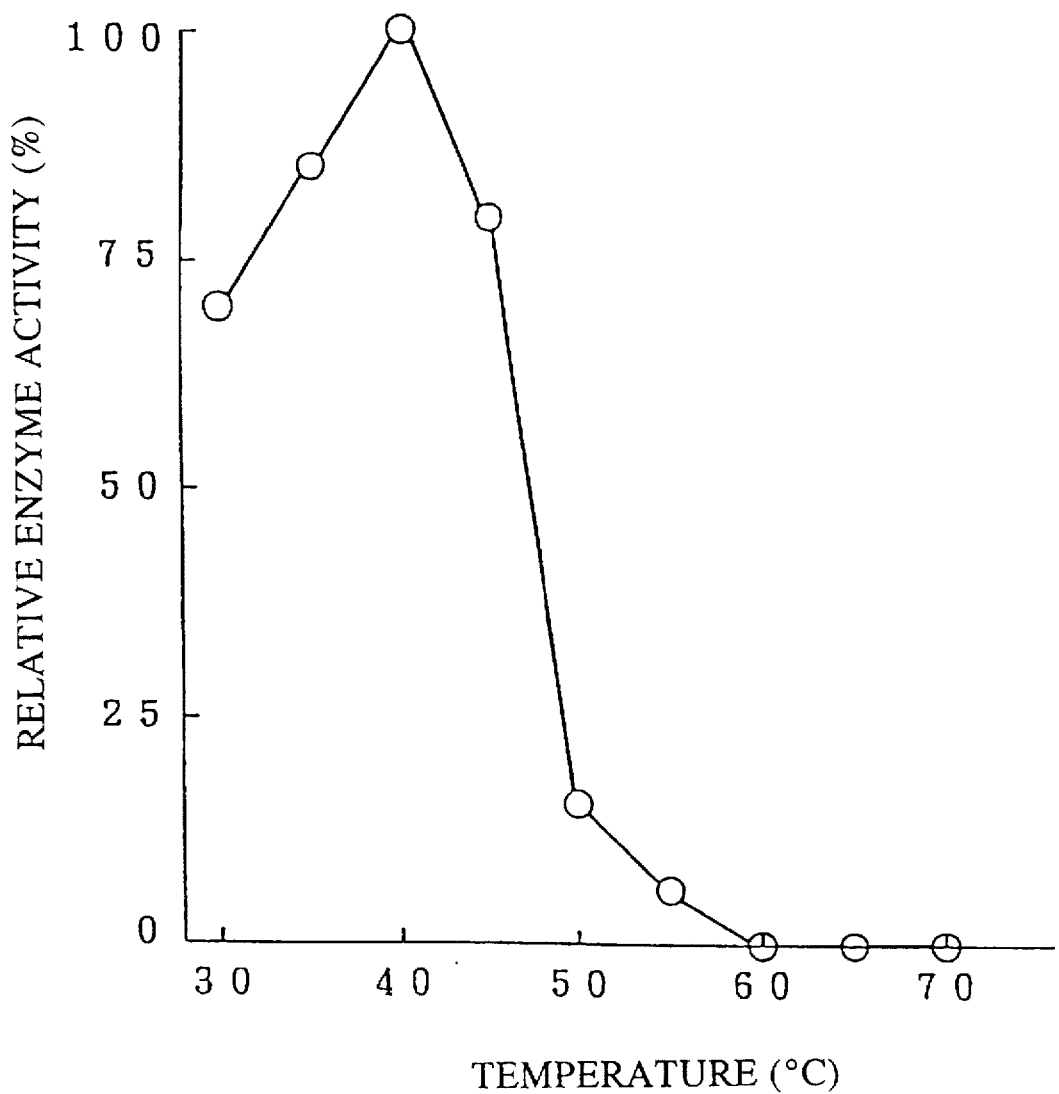
FIG. 1 shows the influence of temperature on the activity of a non-reducing saccharide-forming enzyme derived from *Rhizobium sp.* M-11.

The non-reducing saccharide-forming enzymes usable in the present invention include those which can form α-glycosyltrehalose from one or more reducing amylaceous partial starch hydrolysates selected from those with a glucose polymerization degree of 3 or more which are contained in liquefied starch solutions with a relatively-low DE. Examples of such enzymes are those derived from microorganisms of the genera Rhizobium, Arthrobacter, Brevibacterium, Flavobacterium, Micrococcus, Curtobacterium, Mycobacterium and Terrabacter as disclosed in Japanese Patent Application No.349,216/93. If necessary, thermostable non-reducing saccharide-forming enzymes can be arbitrarily used in the present invention. For example, a thermostable non-reducing saccharide-forming enzyme derived from a microorganism of the genus Sulfolobus as disclosed in Japanese Patent Application No.166,011/94, titled "Thermostable non-reducing saccharide-forming enzyme, and its preparation and uses", applied for by the present applicant on the day of Jun. 24, 1994, can be arbitrarily used. Any enzyme, which specifically hydrolyzes the linkage between a trehalose moiety and others in α-glycosyltrehalose formed by allowing a non-reducing saccharide-forming enzyme to act on a liquefied starch solution, can be used as a trehalose-releasing enzyme in the present invention: For example, those derived from microorganisms of the genera Rhizobium, Arthrobacter, Brevibacterium and Micrococcus as disclosed in Japanese Patent Application No.79,291/94 can be arbitrarily used. If necessary, thermostable trehalose-releasing enzymes such as that derived from a microorganism of the genus Sulfolobus as disclosed in Japanese Patent Application No.166,126/94, applied for by the present applicant on the day of Jun. 25, 1994, can be arbitrarily used in the present invention.

Any enzyme can be arbitrarily used in the present invention as a maltose-trehalose converting enzyme as long as it forms trehalose: Examples of such an enzyme are those derived from microorganisms of the genera Pimerobacter, Pseudomonas and Thermus as disclosed in Japanese Patent Application No.144,092/94, titled "Maltose-trehalose converting enzyme, and preparation and uses thereof", applied for by the present applicant on the day of Jun. 3, 1994. The methods used for preparing the non-reducing saccharide-forming enzymes, trehalose-releasing enzymes, and maltose-trehalose converting enzymes in the present invention are those which comprise culturing microorganisms capable of forming such enzymes in nutrient culture media, and collecting the formed enzymes.

Any nutrient culture medium can be used in the invention as long as those microorganisms can grow therein and form the aforesaid enzymes: For example, synthetic- and natural-nutrient culture media can be used as a nutrient culture medium. Any carbon-containing substance can be used in the invention as a carbon source as long as it is utilized by the microorganisms: For example, saccharides such as glucose, fructose, lactose, sucrose, mannitol, sorbitol, molasses and reducing partial starch hydrolysates; and organic acids such as citric acid, succinic acid, and their salts can be used in the invention. The concentration of these carbon sources in nutrient culture media is appropriately chosen. In the case of using reducing partial starch hydrolysates, it is usually 20% or lower, more particularly, 5% or lower, d.s.b., in view of the growth of microorganisms. The nitrogen sources usable in the invention are, for example, inorganic nitrogen compounds such as ammonium salts and nitrates; and organic nitrogen-containing substances such as urea, corn steep liquor, casein, peptone, yeast extract and beef extract. The inorganic ingredients usable in the invention are, for example, calcium salts, magnesium salts, potassium salts, sodium salts, phosphates and other salts of manganese, zinc, iron, copper, molybdenum and cobalt. If necessary, amino acids and vitamins can be arbitrarily used in combination.

The microorganisms used in the present invention are cultured under aerobic conditions at a temperature, usually, in the range of 4°–40° C., preferably, in the range of 20°–37° C.; and at a pH in the range of 4–10, preferably, in the range of 5–9. In the case of culturing such microorganisms which form thermostable enzymes, the cultivation temperature is usually set to a temperature in the range of 40°–90° C., preferably, 50°–80° C., and the cultivation pH is set to a pH in the range of 2–10, preferably, in the range of 3–9. The cultivation time used in the invention is set to a time longer than that the doubling time of the microorganisms, preferably, 10–100 hours. The concentration of dissolved oxygen (DO) in nutrient culture media is not specifically restricted to, and usually it is set to a level in the range of 0.5–20 ppm. The DO level can be kept within the range by controlling the stirring—and/or aeration-conditions with or without oxygen and/or by increasing the inner pressure of fermenters. The cultivation is carried out batchwise or in continuous manner.

After completion of the culture of microorganisms, the objective enzymes are recovered. Inasmuch as the enzyme activities are found in both cells and cell-free supernatant, they can be used as a crude enzyme. Of course the intact culture can be used as a crude enzyme. Conventional liquid-solid separation methods can be used to remove cells from the culture. For example, methods for directly centrifuging the culture, as well as those for filtrating the culture with precoat filters or for separating cells on membrane filtration with plain filters or follow fibers, can be suitably used. The resultant cell-free filtrates can be used intact as an enzyme solution or may be concentrated prior to use. The concentration methods usable in the invention are, for example, salting out using ammonium sulfate, sedimentation using acetone and/or alcohol, and concentration using membranes such as plain filters and follow fibers.

Cell-free filtrates and their concentrates can be immobilized by conventional immobilization methods. Examples of such methods are conjugation methods using ion exchangers, covalent bondings and absorptions using resins or membranes, and inclusion methods using high-molecular weight substances. Cells separated from the culture can be used as a crude enzyme without any further treatment, or they may be immobilized prior to use. For example, such cells are immobilized by mixing them with sodium alginate, and dropping the resultant mixture in calcium chloride solution to gelatinize the drops into granules. The granules thus obtained can be fixed by treating them with polyethylene imine or glutaraldehyde. Enzyme extracts from cells can be used in the invention as a crude enzyme solution. For example, clear solutions of crude enzymes can be prepared by extracting the objective enzymes from cells by ultrasonic disruption method, mechanical disruption method using glass beads or alumina, or french-press disruption method; and subjecting the resultant extracts to centrifugation or membrane filtration.

The crude enzyme solutions thus obtained can be used intact or after purification by conventional methods. For example, purified enzyme preparations which exhibit a single band on electrophoresis can be prepared by dialyzing crude enzyme preparations prepared by salting out crude enzyme solutions with ammonium sulfate and concentrating the resultant solutions; and successively purifying the dialyzed solutions on anion-exchange column chromatography using "DEAE TOYOPEARL®", an anion-exchange resin; hydrophobic column chromatography using "BUTYL TOYOPEARL®", a hydrophobic resin; and gel filtration chromatography using "TOYOPEARL® HW-55", a resin for gel filtration, all of which are products of Tosoh Corporation, Tokyo, Japan.

The non-reducing saccharide-forming enzymes thus obtained have the following physicochemical properties:

(1) Action

Forming α-glycosyltrehalose when allowed to act on one or more reducing partial starch hydrolysates having a glucose polymerization degree of 3 or more;

(2) Molecular weight

About 76,000–87,000 daltons on sodium dodecylsulfate-polyacrylamide gel electrophoresis (SDS-PAGE);

(3) Isoelectric point (pI)

About 3.6–4.6 on isoelectrophoresis using ampholyte;

(4) Optimum temperature

About 35°–40 C when incubated at pH 7.0 for 60 min;

(5) Optimum pH

About 6.4–7.2 when incubated at 40° C. for 60 min;

(6) Thermal stability

Stable up to a temperature of about 35°–40° C. when incubated at pH 7.0 for 60 min; and (7) pH Stability Stable at a pH in the range of about 5.5–11.0 when incubated at 25° C. for 16 hours.

The activity of the non-reducing saccharide-forming enzymes is assayed as follows: One ml of an enzyme solution is added to 4 ml of 1.25 w/v % maltopentaose in 50 mM phosphate buffer (pH 7.0), and the mixture solution is incubated at 40° C. for 60 min. The reaction mixture is heated at 100° C. for 10 min to suspend the enzymatic reaction, and the reaction mixture is precisely diluted by 10 times with deionized water, followed by determining the reducing power of the diluted solution on the Somogyi-Nelson's method. As a control, an enzyme solution, which had been heated at 100° C. for 10 min to inactivate the enzyme, is treated similarly as above. One unit activity of the present enzyme is defined as the amount of enzyme which eliminates the reducing power of that of one micromole of maltopentaose per minute.

The trehalose-releasing enzymes usable in the present invention generally have the following physicochemical properties:

(1) Action

Specifically hydrolyzing the linkage between a trehalose moiety and other glycosyl moiety;

(2) Molecular weight

About 57,000–68,000 daltons on sodium dodecylsulfate-polyacrylamide gel electrophoresis (SDS-PAGE);

(3) Isoelectric point (pI)

About 3.3–4.6 on isoelectrophoresis using ampholyte;

(4) Optimum temperature

About 35°–45° C. when incubated at pH 7.0 for 30 min;

(5) Optimum pH

About 6.0–7.5 when incubated at 40° C. for 30 min;

(6) Thermal stability

Stable up to a temperature of about 35°–45° C. when incubated at pH 7.0 for 60 min; and (7) pH Stability Stable at a pH in the range of about 5.0–10.0 when incubated at 25° C. for 16 hours.

The activity of the trehalose-releasing enzymes is assayed as follows: One ml of an enzyme solution is added to 4 ml of 1.25 w/v % maltotriosyl trehalose alias α-maltotetraosyl α-D-glucoside in 50 mM phosphate buffer (pH 7.0), and the mixture solution is incubated at 40° C. for 30 min. To the resultant reaction mixture is added a copper solution for the Somogyi reaction to suspend the enzymatic reaction, followed by the determination of the reducing power on the Somogyi-Nelson's method. As a control, an enzyme solution, which was preheated at 100° C. for 10 min to inactivate the enzyme, is assayed similarly as above. One unit activity of the enzyme is defined as the amount of enzyme which increases the reducing power of that of one μmole of glucose per minute when assayed with the above-mentioned assay.

The maltose-trehalose releasing enzymes usable in the present invention have the following physicochemical properties:

(1) Action

Converting maltose into trehalose, and vice versa;

(2) Molecular weight

About 57,000–120,000 daltons on sodium dodecylsulfate-polyacrylamide gel electrophoresis (SDS-PAGE);

(3) Isoelectric point (pI)

About 3.8–5.1 on isoelectrophoresis using ampholyte;

(4) Inhibition

Being inhibited by 1 mM $Cu_{++}$, 1 mM $Hg_{++}$ and 50 mM Tris-HCl buffer; and (5) Origin Microorganism origin.

The activity of the maltose-trehalose converting enzymes is assayed as follows: One ml of an enzyme solution is added to one ml of 20 w/v % maltose as a substrate in 10 mM phosphate buffer (pH 7.0), and the mixture solution is incubated at 25° C. for 60 min, followed by heating the solution at 100° C. for 10 min to suspend the enzymatic reaction. To the resultant reaction mixture is precisely diluted by 11-fold with 50 mM phosphate buffer (pH 7.5), and 0.4 ml of the diluted solution is admixed with 0.1 ml of an enzyme solution containing one unit/ml trehalase. The resultant solution is incubated at 45° C. for 120 min, followed by determining the amount of glucose by the glucose-oxidase method. As a control, by using trehalase and an enzyme solution, which were preheated at 100° C. for 10 min to inactivate the enzymes, the resultant enzyme solution is assayed similarly as above. With the above assay, the content of trehalose, formed by the maltose-trehalose converting enzyme, is determined based on the amount of the formed glucose, and one unit activity of the enzyme is defined as the amount of enzyme which forms one pmole of trehalose per minute.

The starch debranching enzymes usable in the present invention include those which act on liquefied starch solutions with a relatively-low DE, preferably, lower than DE 15, and hydrolyze the debranching points of starch. For example, well known pullulanase and isoamylase, as well as commercially available enzyme preparations thereof, can be arbitrarily used in the present invention. The cyclomaltodextrin glucanotransferase usable in the present invention includes those which act on liquefied starch solutions with a relatively-low DE, preferably, lower than DE 15, and transfer amylaceous saccharides to their receptors, i.e. those which have a reaction mechanism of disproportionation reaction. Examples of such enzymes arbitrarily used in the present invention are those derived from known microorganisms of the genera Bacillus and Klebsiella, as well as commercially available enzyme preparations thereof.

In addition to the starch debranching enzymes and/or cyclomaltodextrin glucanotransferases, other amylases, preferably, those which act on liquefied starch solutions with a relatively-low DE to form mainly oligosaccharides having a glucose polymerization degree of 3 or more, can be arbitrarily used in the present invention. Examples of such amylases are α-amylase, maltotriose-forming enzyme, maltotetraose-forming enzyme, maltopentaose-forming enzyme, maltohexaose-forming enzyme and maltoheptaose-forming enzyme.

The starch usable in the present invention includes seeds and swollen stems such as corn starch, rice starch and wheat starch, and roots such as potato starch, sweet potato starch and tapioca starch. To liquefy the starch, it is suspended in water, preferably, into a solution of 10% or more, more preferably, a solution of about 20–50%, d.s.b., and the suspension is liquefied by heating, acids or enzymes. The liquefaction degree is suitably set to a relatively-low level, preferably, to a DE less than 15, more preferably, to a DE less than 10. In the case of liquefying starch with acids, it is effected by hydrochloric acid, phosphoric acid and/or oxalic acid, and the resultant liquefied starch is adjusted to a prescribed pH level with carbonate calcium, calcium oxide and/or sodium carbonate prior to use. In the case of liquefying starch with enzymes, α-amylases, particularly, thermostable liquefying α-amylases are satisfactorily used.

The liquefied starch solutions thus obtained can be subjected to the action of a non-reducing saccharide-forming enzyme together with a starch debranching enzyme and/or a cyclomaltodextrin glucanotransferase, or to the action of a non-reducing saccharide-forming enzyme and a trehalose-releasing enzyme together with a starch debranching enzyme and/or a cyclomaltodextrin glucanotransferase under the pH—and temperature-conditions which allow these enzymatic reactions to proceed, for example, a pH of 4–10, preferably, of 5–8, and a temperature of about 10°–80° C., preferably, of about 30°–70° C. The order of the enzymes to be added to the liquefied starch solutions is not specifically restricted to, for example, one or more of these enzymes can be first added to the solutions, then the remaining enzyme(s) is added to, or all the enzymes can be added to at the same time.

The amounts of the enzymes to be added can be chosen depending upon the enzymatic conditions and reaction times. Usually, they are chosen from (i) about 0.01–100 units/g substrate, d.s.b., in liquefied starch solutions for the enzymatic reaction of a non-reducing saccharide-forming enzyme and a trehalose-releasing enzyme, (ii) about 1–10,000 units/g substrate, d.s.b., for starch debranching enzymes, and (iii) about 0.05–500 units/g substrate, d.s.b., for cyclomaltodextrin glucanotransferases. The resultant saccharide compositions with a reduced reducibility, which comprise non-reducing saccharides and reducing amylaceous saccharides, are prepared by subjecting liquefied starch solutions to the action of starch debranching enzymes and/or cyclomaltodextrin glucanotransferases and non-reducing saccharide-forming enzymes together with or without trehalose-releasing enzymes so that the saccharide compositions have characters that they contain trehalose in quantity or considerably-large amounts of relatively-low molecular weight α-glycosyltrehalose and/or α-glycosyl α-glycoside, and that they can be arbitrarily used as a material saccharide composition with a reduced reducibility in the present invention. The α-glycosyl α-glycoside is a name given to a compound such as α-D-oligoglycosyl α-D-oligoglucoside as disclosed in Japanese Patent Application No.54,377/94 applied for by the present applicant.

The reaction mixtures obtained by the aforesaid enzymatic reactions are in usual manner filtered and centrifuged to remove impurities, then the resultant solutions are decolored with an activated charcoal, desalted and purified with ion-exchange exchange resins in H—and OH-form and concentrated into syrupy products which may be further dried into powdery products. If necessary; the syrupy products can be purified by one or more fractionation methods of column chromatography such as ion-exchange column chromatography, column chromatography using activated charcoals or silica gels; separation methods using organic solvents such as alcohols or acetone; and membrane separations using membranes with an appropriate separability. Thus, the material saccharide compositions used in the present invention, having a reduced reducibility and an increased content of non-reducing saccharides, are readily prepared.

The industrial-scale preparations for such preparations used in the present invention include ion-exchange column chromatography, for example, column chromatography using strong-acid cation exchange resins as disclosed in Japanese Patent Laid-Open Nos. 23,799/83 and 72,598/83 can be arbitrarily used to remove concomitant saccharides to obtain the material saccharides usable in the present invention. In this case, fixed bed—, moving bed—and pseudo moving bed-methods can be arbitrarily used.

If necessary, the resultant saccharide compositions with a reduced reducibility, which contain non-reducing saccharides having a trehalose structure, can be further processed into the material saccharide composition with a reduced reducibility used in the present invention by hydrolyzing them with amylases such as α-amylase, β-amylase, glucoamylase or α-glucosidase to control their sweetness and/or lower their viscosity.

The saccharide compositions thus obtained can be arbitrarily used as a material saccharide composition in the present invention. For example, those rich in non-reducing saccharides consisting of trehalose and saccharides having a trehalose structure, i.e. those which contain 20% or more, preferably, 40% or more, more preferably, 60% or more of trehalose, d.s.b., and have a relatively-low DE, usually, a DE less than 70, preferably, a DE less than 50, more preferably, a DE less than 30, are satisfactorily used. Varying dependently on their compositions, the material saccharide compositions used in the present invention have features that they have a relatively-low DE regardless of their large amount of non-reducing reducing saccharides, relatively-low molecular weight substances to be tasted, and relatively-low viscosity, and that they facilitate the hydrogenation and the subsequent processes such as purification and concentration wherein the amount of hydrogen which is required for the hydrogenation is reduced by a large margin.

Any method for hydrogenating the resultant saccharide compositions with a reduced reducibility, which comprise reducing saccharides and non-reducing saccharides consisting of trehalose and/or saccharides having a trehalose structure, can be used in the present invention as long as it does not decompose the non-reducing saccharides but hydrogenates saccharides into sugar alcohols. For example, the material saccharide compositions are prepared into 30–70% aqueous solutions, transferred to an autoclave, mixed with about 8–10% Raney nickel as a catalyst, and heated up to a temperature of 90°–150° C. under stirring conditions to terminate the hydrogenation or, preferably, to partially hydrogenate the contents until they show a DE less than 0.5, followed by removing the Raney nickel. The resultant mixtures were decolored with an activated charcoal in usual manner, desalted with an ion-exchange resin, and concentrated into syrupy products. If necessary, the syrupy products are arbitrarily dried into powdery products, or crystallized into crystalline powders containing trehalose crystal. The resultant saccharide compositions with a reduced reducibility contain non-reducing saccharides, which consist of trehalose and/or non-reducing saccharides having a trehalose structure, such as α-glycosyltrehalose and α-glycosyl α-glycoside, and one or more sugar alcohols such as sorbitol, maltitol, maltotriitol, maltotetraiol and maltopentaitol.

The saccharide compositions with a reduced reducibility according to the present invention have an extremely reduced reducibility and a satisfactory stability, and can be freely mixed and processed with amino acid-containing substances such as amino acids, oligopeptides and proteins without substantial fear of causing unsatisfactory browning and disagreeable smell, and of deteriorating the inherent properties of the material substances. In spite of their relatively-low reducibility, the saccharide compositions have a relatively-low viscosity, and those with a considerably-low glucose polymerization degree have a satisfactorily-high quality and sweetness.

The saccharide compositions according to the present inventions form relatively-low molecular weight non-reducing oligosaccharides and maltooligosaccharides when hydrolyzed with amylases such as α-amylase derived from pancreas. The oligosaccharides are readily hydrolyzed with α-glucosidase and enzymes in small intestines into glucose and trehalose which is then readily hydrolyzed with trehalase into glucose molecules. Thus, the present saccharide compositions are readily assimilated, absorbed and utilized by living bodies when orally administered. Furthermore, they are not substantially fermented by dental carries-inducing microorganisms, and this renders them useful as a dental carries-preventing sweetener.

With their satisfactory stability, the saccharide compositions rich in a crystal form can be arbitrarily used by processing them with binders such as pullulan, hydroxy ethyl starch and/or polyvinylpyrrolidone into sugar coated agents in a tablet form. They also have features of osmosis-controlling activity, filler-imparting ability, gloss-imparting activity, moisture-retaining activity, viscosity-imparting activity, crystallization-preventing activity for other sweeteners, substantial non-fermentability, and retrogradation-preventing activity for gelatinized starch.

The present saccharide compositions can be arbitrarily used as a sweetener, taste-improving agent, quality-improving agent, stabilizer, excipient, filler and diluent in a variety of compositions such as food products, tobaccos, cigarettes, feeds, pet foods, cosmetics and pharmaceuticals.

The present saccharide compositions can be used intact as a seasoning for sweetening. If necessary, they can be used together with adequate amounts of one or more other sweeteners, for example, a powdered syrup, glucose, maltose, sucrose, isomerized sugar, honey, maple sugar, isomaltooligosaccharide, galactooligosaccharide, fructooligosaccharide, lactosucrose, sorbitol, maltitol, lactitol, dihydrocharcone, stevioside, α-glycosyl stevioside, rebaudioside, glycyrrhizin, L-aspartyl L-phenylalanine methyl ester, saccharin, glycine and alanine; and/or a filler such as dextrin, starch and lactose.

The present saccharide compositions, particularly, those rich in a crystal form, can be used intact, or, if necessary they can be mixed with an excipient, filler, diluent and binder and formed into granules, spheres, shot-rods, plates, cubes and tablets, prior to use.

The present saccharide compositions have the following features: (i) They have a sweetness which well harmonizes with other materials with sourness, acidity, saltiness, bitterness, astringency and deliciousness; and (ii) they are highly acid- and heat-tolerance. Thus, they can be favorably used in food products in general as a sweetener, taste-improving agent and quality-improving agent.

The present saccharide compositions can be used in seasonings such as amino acids, peptides, soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuk-no-moto" (an instant mix for Chinese dish), "tentsuyu" (a sauce for Japanese deep-fat fried food), "ment-suyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), nucleic acid condiments, mixed seasoning, "mirin" (a sweet sake), "shin-mirin" (a synthetic mirin), table sugar and coffee sugar.

Also, the present saccharide compositions can be freely used for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettaraα-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ikα-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki"

(a tangle roll); milk products such as yoghurt and cheese; canned and bottled products such as those of meat, fish meat, fruit and vegetable; alcoholic beverages such as sake, synthetic sake, wine, liqueur and liquor; soft drinks such as coffee, tea, cocoa, juice, carbonated beverage, sour milk beverage and beverage containing a lactic acid bacterium; instant food products such as instant pudding mix, instant hot cake mix and "sokuseki-shiruco" (an instant mix of adzuki-bean soup with rice cake) and instant soup mix; and beverages such as baby foods, foods for therapy, beverages supplemented with nutrition, peptide foods and frozen foods; as well as for improving the tastes and qualities of the aforementioned food-products.

The present saccharide compositions can be also used in feeds and pet foods for animals such as domestic animals, poultry, honey bees, silk warms and fishes to improve their taste preferences, and further can be arbitrarily used as a sweetener, taste-improving agent, quality-improving agent and stabilizer in other products in a paste or liquid form such as a tobacco, cigarette, dentifrice, lipstick, rouge, lip cream, internal medicine, tablet, troche, cod liver oil in the form of drop, cachou, oral refrigerant, gargle, cosmetic and pharmaceutical.

The present saccharide compositions can be used as a quality-improving agent and stabilizer in biologically active substances which are susceptible to lose their effective ingredients and activities, as well as in health foods and pharmaceuticals containing biologically active substances. Examples of such biologically active substances are lymphokines such as α-, β- and γ-interferons (IFNs), tumor necrosis factor-α(TNF-α), tumor necrosis factory-β(TNF-β), macrophage migration inhibitory factor, colony-stimulating factor, transfer factor and interleukin 2; hormones such as insulin, growth hormone, prolactin, erythropoietin and follicle-stimulating hormone;

biological preparations such as BCG vaccine, Japanese encephalitis vaccine, measles vaccine, live polio vaccine, smallpox vaccine, tetanus toxoid, . Trimeresurus antitoxin and human immunoglobulin; antibiotics such as penicillin, erythromycin, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease, β-amylase, isoamylase, glucanase and lactase; extracts such as ginseng extract, snapping turtle extract, chlorella extract, aloe extract and propolis extract; viable microorganisms such as viruses, lactic acid bacteria and yeasts; and other biologically active substances such as a royal jelly. By using the present saccharide compositions, the aforesaid biologically active substances are arbitrarily formed into health foods and pharmaceuticals with a satisfactorily-high stability and quality without fear of losing or inactivating their effective ingredients and their activities.

As is described above, the methods to incorporate the present saccharide compositions into the aforesaid compositions include conventional ones, for example, mixing, kneading, dissolving, melting, soaking, permeating, sprinkling, applying, coating, spraying, injecting, crystallizing and solidifying. The saccharide compositions according to the present invention are usually incorporated into the above-mentioned compositions in an amount of 0.1% or more, preferably, one % or more, d.s.b.

The following experiments explain the present invention in more detail.

Firstly, non-reducing saccharide-forming enzymes derived from microorganisms of *Rhizobium sp.* M-11 and *Arthrobacter sp.* Q36 are explained, and secondary, other such enzymes derived from known microorganisms are explained:

EXPERIMENT 1
Production of non-reducing saccharide-forming enzyme by Rhizobium so. M-11

A liquid nutrient culture medium, consisting of 2.0 w/v % maltose, 0.5 w/v % peptone, 0.1 w/v % yeast extract, 0.1 w/v % disodium hydrogenphosphate, 0.1 w/v % potassium hydrogenphosphate and water, was adjusted to pH 7.0, and about 100 ml aliquots of which were placed in 500-ml Erlenmeyer flasks, autoclaved at 120° C. for 20 minutes to effect sterilization, cooled, inoculated with a stock culture of *Rhizobium sp.* M-11 (FERM BP-4130), and incubated at 27° C. for 24 hours under stirring conditions of 130 rpm. The resultant cultures were pooled for a seed culture.

About 20 L of a fresh preparation of the same nutrient culture medium used in the above culture was placed in a 30-L fermenter, sterilized by heating, cooled to 30° C. and inoculated with one w/v % of the seed culture, followed by the incubation at 30° C. and pH 6.0–8.0 for about 24 hours under stirring—and aerobic-conditions. The resultant culture had an enzyme activity of about 1.5 units/ml. A portion of the culture was centrifuged to separate into cells and a culture supernatant, and the cells were suspended in 50 mM phosphate buffer (pH 7.0) to give the same volume of the portion. The enzyme activities of the cell suspension and the culture supernatant were assayed revealing that they were respectively about 0.6 units/ml and about 0.9 units/ml.

EXPERIMENT 2
Purification of enzyme

An about 18 L of the culture obtained in Experiment 1 was treated to disrupt cells with "MINI-RABO", a supper high-pressure cell disrupter commercialized by Dainippon Pharmaceutical Co., Ltd., Tokyo, Japan. The resultant suspension was centrifuged at 10,000 rpm for 30 min to obtain an about 16 L supernatant. Ammonium sulfate was added to and dissolved in the supernatant to give a saturation degree of 0.2, and the resultant solution was allowed to stand at 4° C. for one hour and centrifuged to obtain a supernatant.

Ammonium sulfate was dissolved in the supernatant to give a saturation degree of 0.6, and the resultant solution was centrifuged to obtain a precipitate which was then dissolved in 10 mM phosphate buffer (pH 7.0). The resultant solution was dialyzed against a fresh preparation of the same phosphate buffer at 4° C. for 24 hours, and centrifuged to remove insoluble substances. Three hundred and sixty ml of the resultant dialyzed solution was divided into 2 portions which were then separately subjected to column chromatography using a column packed with 300 ml of "DEAE-TOYOPEARL®", an ion exchanger commercialized by Tosoh Corporation, Tokyo, Japan.

The objective enzyme was adsorbed on the ion exchanger, and eluted therefrom with a fresh preparation of the same phosphate buffer supplemented with salt. The resultant fractions having the objective enzyme activity were pooled, and dialyzed against a fresh preparation of the same phosphate buffer supplemented with 2 M ammonium sulfate. The dialyzed solution thus obtained was centrifuged to remove insoluble substances, and the resultant supernatant was subjected to hydrophobic column chromatography using a column packed with 300 ml of "BUTYL-TOYOPEARL® 650", a hydrophobic gel commercialized by Tosoh Corporation, Tokyo, Japan. The enzyme adsorbed on the gel was eluted from the column with a liner gradient buffer ranging from 2M to 0M, followed by recovering fractions with the enzyme activity. The resultant fractions were pooled and subjected to gel filtration chromatography using "TOYOPEARL® HW-55", a resin for gel chromatography commercialized by Tosoh Corporation, Tokyo, Japan, followed by recovering fractions with the enzyme activity. The enzyme activity, specific activity and yield in each purification step are in Table 1.

TABLE 1

| Purification step | Enzyme activity (unit) | Specific activity (units/mg protein) | Yield (%) |
|---|---|---|---|
| Culture | 26,800 | — | 100 |
| Supernatant after cell disruption | 20,300 | 0.10 | 76 |
| Dialyzed solution after salting out with ammonium sulfate | 16,100 | 0.32 | 60 |
| Eluate from ion-exchange column | 11,300 | 5.5 | 42 |
| Eluate from hydrophobic column | 5,730 | 98 | 21 |
| Eluate from gel filtration column | 3,890 | 195 | 15 |

A purified enzyme preparation, obtained as an eluate from the gel filtration column in Table 1, was determined for purity on electrophoresis in a 7.5% polyacrylamide gel to show a single protein band, and this meant that the preparation was an electrophoretically homogeneous enzyme with a relatively-high purity.

EXPERIMENT 3
Property of enzyme

The purified enzyme preparation obtained in Experiment 2 was electrophoresed in a 10% sodium dodecylsulfate polyacrylamide gel revealing that the molecular weight was about 77,000–87,000 daltons by comparing it with those of marker proteins commercialized by Japan Bio-Rad Laboratories, Tokyo, Japan.

The purified enzyme preparation was isoelectrophoresed in a polyacrylamide gel containing 2 v/v % "AMPHOLINE", an ampholyte commercialized by Pharmacia LKB Biotechnology AB, Uppsala, Sweden. The resultant gel was sliced into pieces, and a gel piece containing the enzyme was determined for pH revealing that the enzyme has a pI of about 3.6–4.6.

Figure 2:
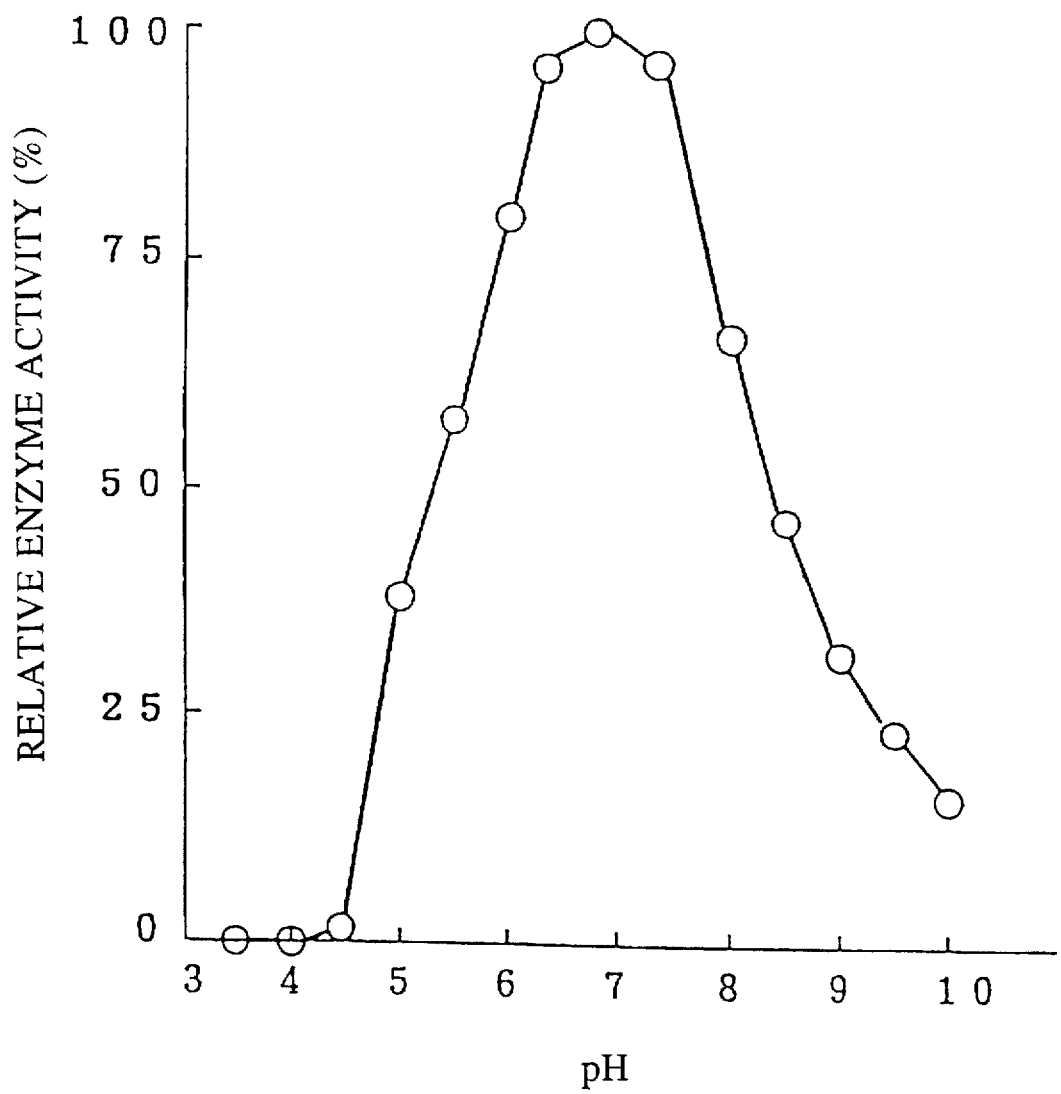
FIG. 2 shows the influence of pH on the activity of a non-reducing saccharide-forming enzyme derived from *Rhizobium sp.* M-11.
Figure 3:
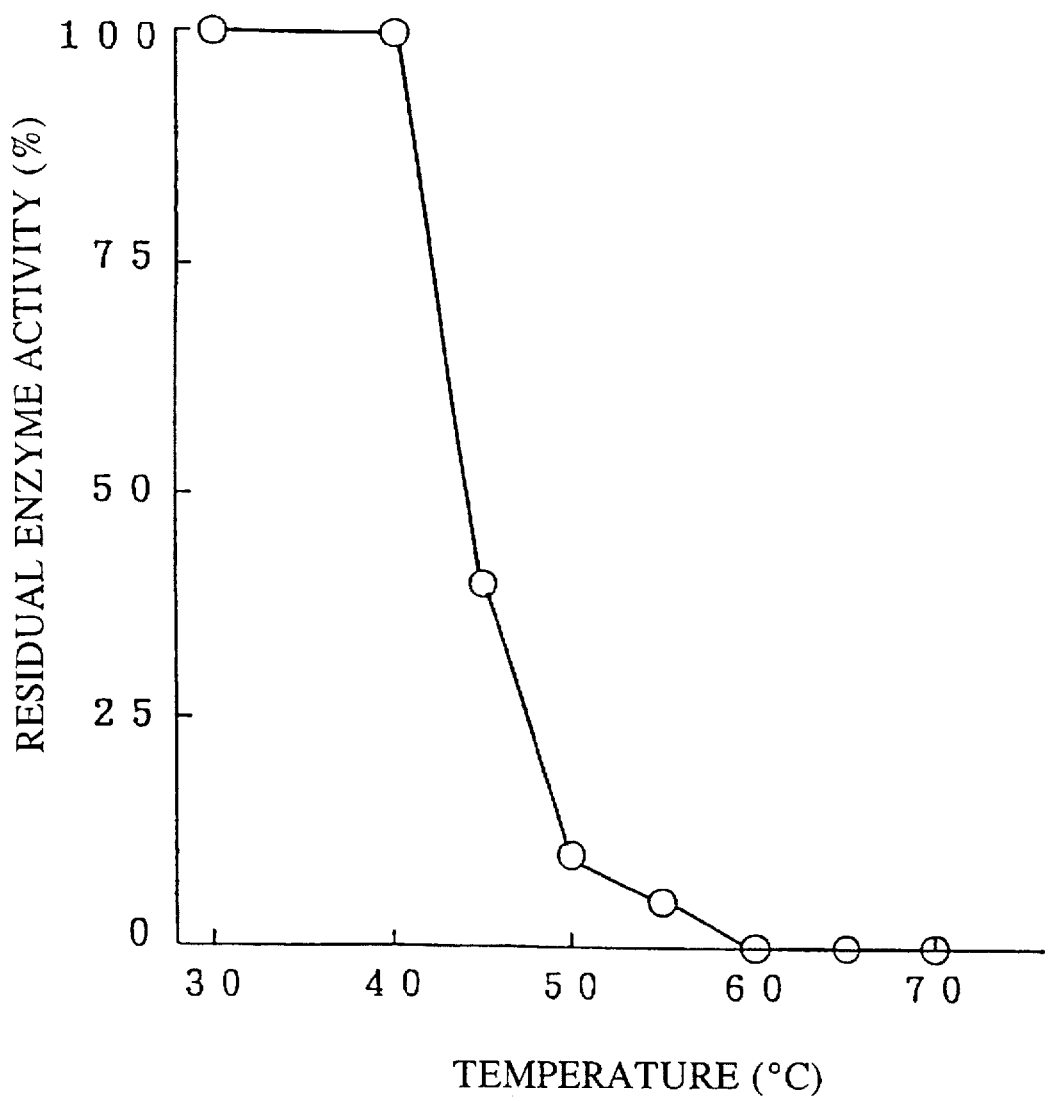
FIG. 3 shows the thermal stability of a non-reducing saccharide-forming enzyme derived from *Rhizobium sp.* M-11.
Figure 4:
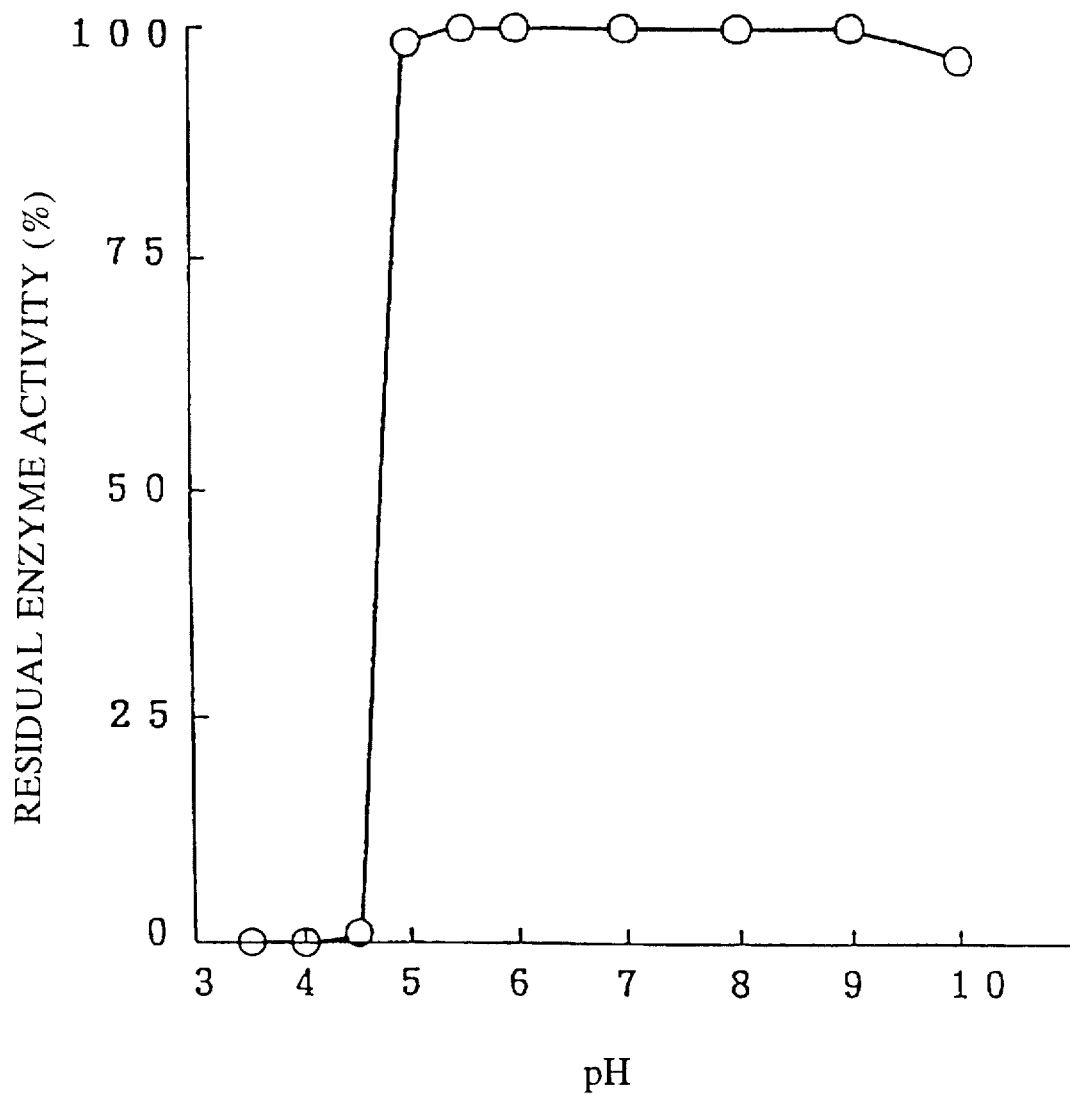
FIG. 4 shows the pH stability of a non-reducing saccharide-forming enzyme derived from *Rhizobium sp.* M-11.
Figure 5:
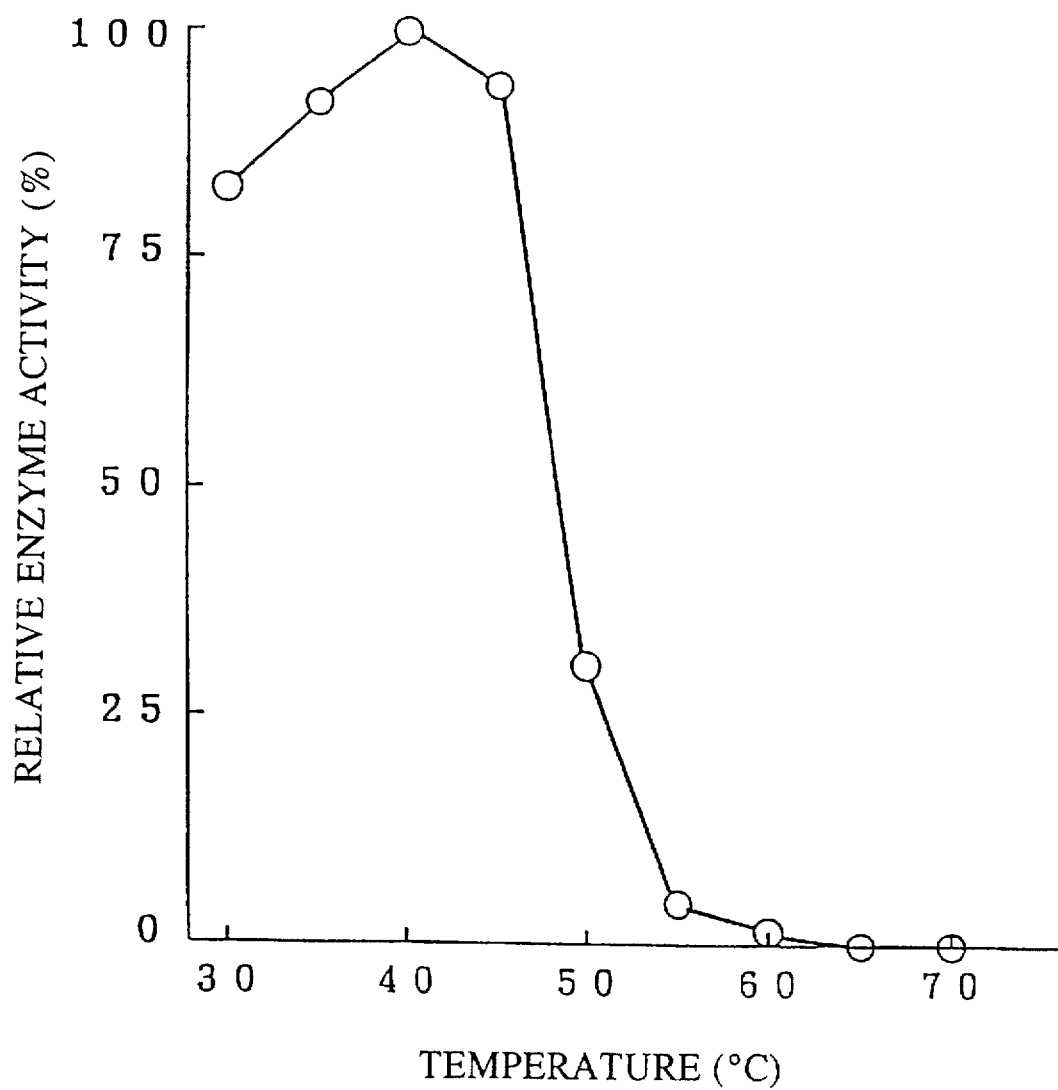
FIG. 5 shows the influence of temperature on the activity of a non-reducing saccharide-forming enzyme derived from *Arthrobacter sp.* Q36.
Figure 6:
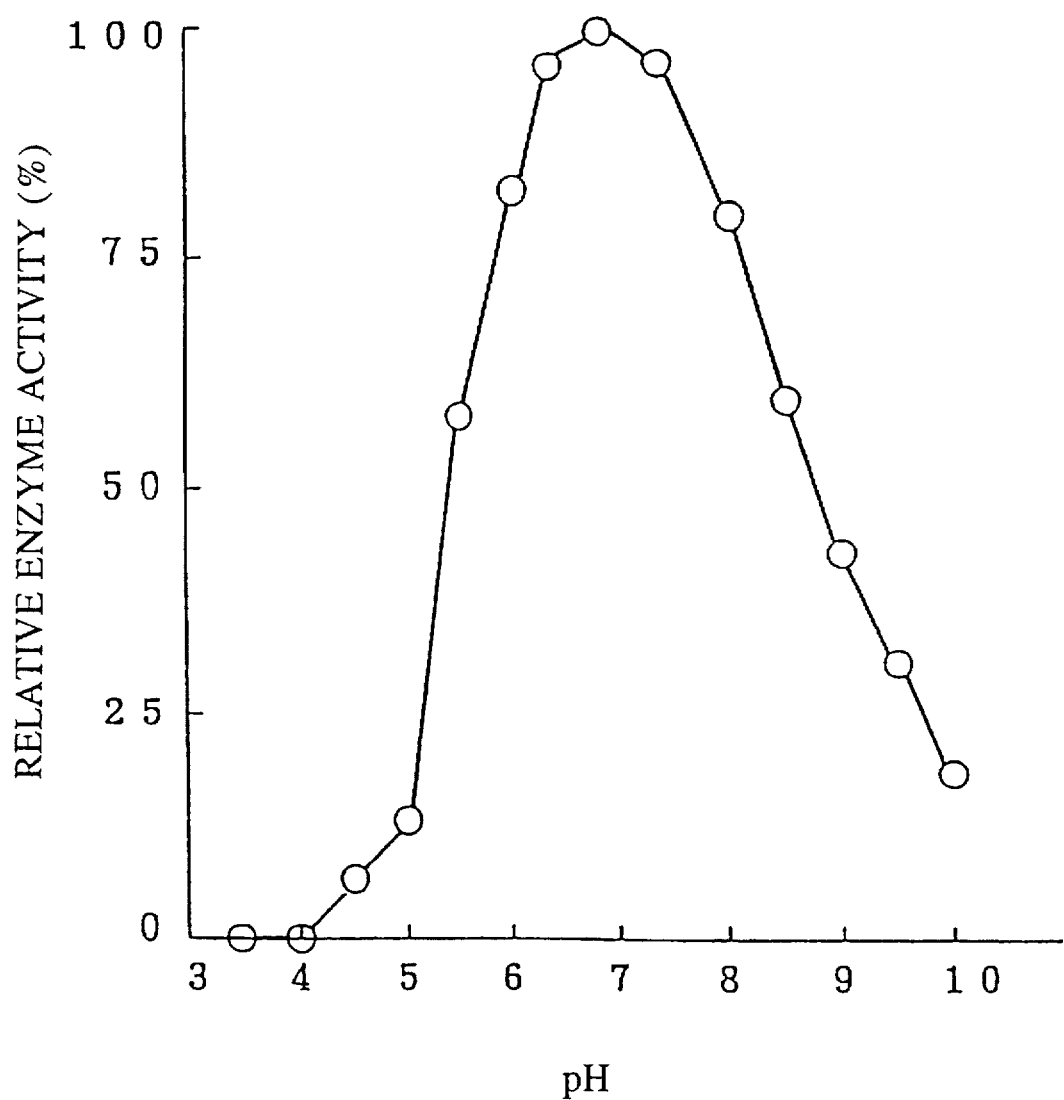
FIG. 6 shows the influence of pH on the activity of a non-reducing saccharide-forming enzyme derived from *Arthrobacter sp.* Q36.
Figure 7:
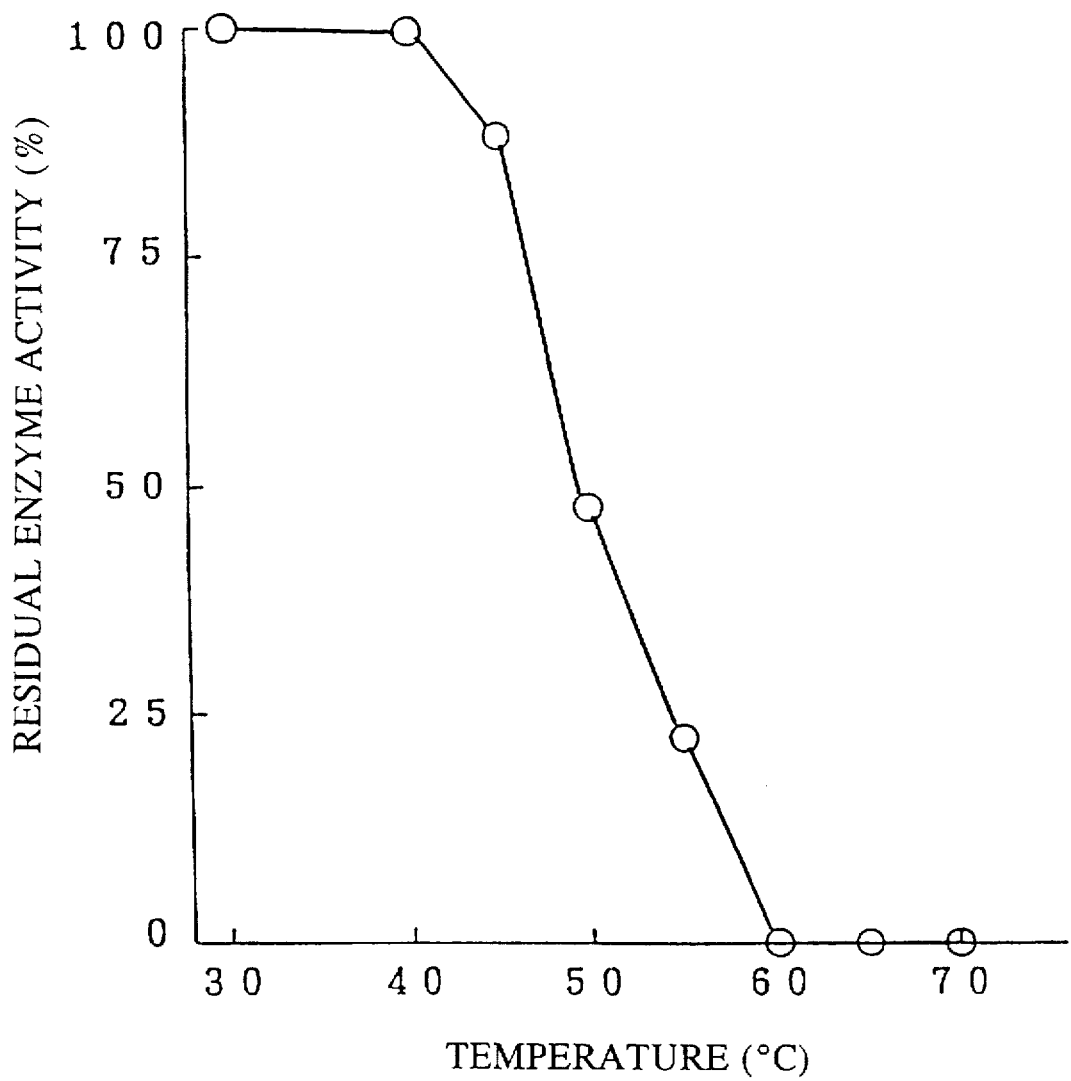
FIG. 7 shows the thermal stability of a non-reducing saccharide-forming enzyme derived from *Arthrobacter sp.* Q36.
Figure 8:
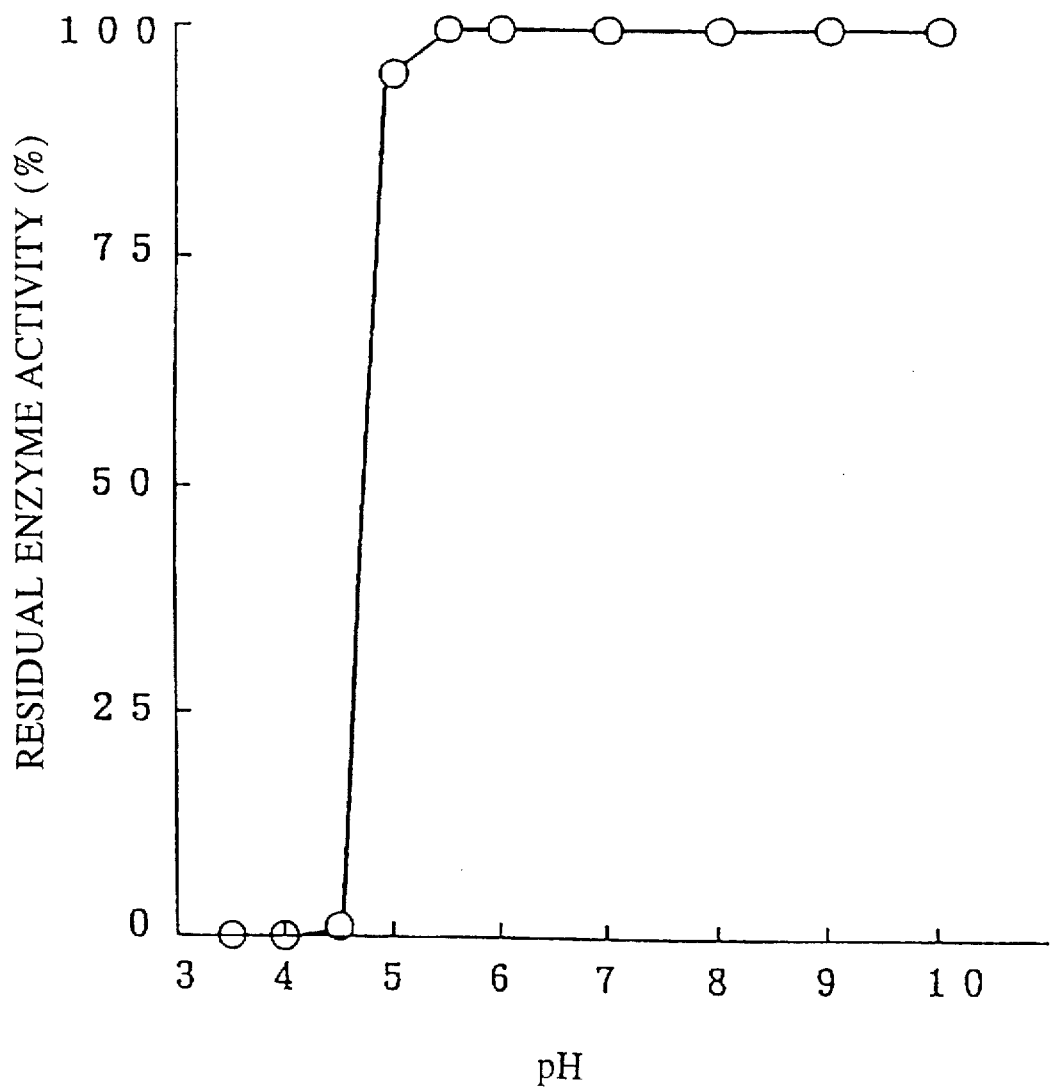
FIG. 8 shows the pH stability of a non-reducing saccharide-forming enzyme derived from *Arthrobacter sp.* Q36.

Effects of temperature and pH on the enzyme activity were studied in accordance with the assay used for the enzyme activity. These results were respectively in FIGS. 1 and 2. The optimum temperature of the enzyme was about 40° C. when incubated at pH 7.0 for 60 min, while the optimum pH was about 7.0 when incubated at 40° C. for 60 min. The thermal stability of the enzyme was determined by incubating it in 50 mM phosphate buffers (pH 7.0) at different temperatures for 60 min, cooling the buffers, and assaying the remaining enzyme activity in each buffer. The pH stability of the enzyme was determined by incubating it in 50 mM phosphate buffers having different pHs at 25° C. for 16 hours, adjusting the buffers to pH 7, and assaying the remaining enzyme activity in each buffer. The results of thermal stability and pH stability were respectively in FIGS. 3 and 4. The enzyme was stable up to a temperature of about 40° C. and stable at a pH of about 6–9.

EXPERIMENT 4
Preparation of non-reducing saccharide

An aqueous solution containing 20 w/v % glucose, maltose, maltotriose, maltotetraose, maltopentaose, maltohexaose or maltoheptaose as a substrate was prepared, and mixed with 2 units/g substrate, d.s.b., of the purified enzyme preparation obtained in Experiment 2, and the resultant mixture was subjected to an enzymatic reaction at 40° C. and pH 7.0 for 48 hours. The reaction mixture was desalted and analyzed on high-performance liquid chromatography (HPLC) using "WAKOBEADS WB-T-330 COLUMN", a product of Wako Pure Chemical Industries Ltd., Tokyo, Japan. The HPLC procedure was conducted at ambient temperature and a flow rate of 0.5 ml/min of water as an eluent, and "RI-8012", a differential refractometer commercialized by Tosho Corporation, Tokyo, Japan, was used for analyzing reaction products.

The results are in Table 2.

TABLE 2

| Substrate | Product | Elution time on HPLC (min) | Percentage (%) |
|---|---|---|---|
| Glucose | Glucose | 33.4 | 100.0 |
| Maltose | Maltose | 28.5 | 100.0 |
| Maltotriose | P I | 23.3 | 35.0 |
| | Maltotriose | 25.9 | 65.0 |
| Maltotetraose | P II | 21.6 | 85.6 |
| | Maltotetraose | 24.1 | 14.4 |
| Maltopentaose | P III | 19.7 | 92.7 |
| | Maltopentaose | 22.6 | 7.3 |
| Maltohexaose | P IV | 18.7 | 93.5 |
| | Maltohexaose | 21.4 | 6.5 |
| Maltoheptaose | P V | 17.8 | 93.4 |
| | Maltoheptaose | 21.0 | 6.7 |

Note: In the Table, the symbols "P I", "P II", "P III", "P IV" and "P V" mean saccharides newly formed from the respective substrates of maltotriose, maltotetraose, maltopentaose, maltohexaose and maltoheptaose.

As is evident from the results in Table 2, each reaction product substantially consists of the remaining substrate and a newly formed saccharide P I, P II, P III, P IV or P V, and other saccharides were not substantially detected. It was revealed that the yields of P II, P III, P IV and P V, which have a glucose polymerization degree of 4 or more, were high, i.e. a yield of 85% or more, d.s.b., while the yield of P I, which has a glucose polymerization degree of 3 or more, was relatively low. It was also revealed that no saccharide is formed from glucose and maltose.

In order to purify the newly formed saccharides in each reaction mixture, the saccharides were column chromatographed on "XT-1016 (polymerization degree of 4%)", a strong-acid action exchange resin in $Na_+$-form commercialized by Tokyo Organic Chemical Industries, Ltd., Tokyo, Japan. The resin was packed in 3 jacketed-stainless steel columns, having an inner diameter of 2.0 cm and a length of one m each, and the columns were cascaded in series, fed with a 5 v/v % reaction mixture containing saccharides against the resin while the inner column temperature was keeping at 55° C., and eluted with 55° C. hot water at a flow rate of SV (space velocity) 0.13 to obtain a high-purity saccharide fraction containing 97% or more of a novel saccharide, d.s.b. The fraction was dried in vacuo to obtain a high-purity preparation of a novel saccharide. The yields of P I, P II, P III, P IV and P IV were respectively about 9%, 65%, 82%, 80% and 77%, d.s.b., with respect to their material saccharides. The purities of P I, P II, P III, P IV and P V were respectively about 97.5%, 98.6%, 99.5%, 98.4% and 98.4%, d.s.b.

The reducing powders of these novel high-purity saccharides were determined on the Somogyi-Nelson's method and expressed by DE. The results are in Table 3.

TABLE 3

| Saccharide preparation | Purity (%) | DE |
|---|---|---|
| P I | 97.5 | 0.83 |
| P II | 98.6 | 0.35 |
| P III | 99.5 | 0.10 |
| P IV | 98.4 | 0.27 |
| P V | 98.4 | 0.23 |

As is evident from the results in Table 3, each saccharide preparation only showed a slight reducing power. It was estimated that such a slight reducing power was due to the remaining reducing maltooligosaccharides originated from the substrates, and this concluded that the newly formed saccharides were substantially free from reducibility.

EXPERIMENT 5
Maillard reaction

A solution, containing one % glycine and 10% of a saccharide preparation PI, P II, P III, P IV or P V in Experiment 4 and 50 mM phosphate buffer (pH 7.0), was kept at 100° C. for 90 min, followed by cooling the resultant solution, and determining for absorbance at a wave length of 480 nm in a 1-cm cell. As a control, maltotriose, maltotetraose, maltopentaose, maltohexaose and maltoheptaose, as a material for the saccharide preparations, were similarly treated as above, and measured for absorbance at a wave length of 480 nm. The results are in Table 4.

TABLE 4

| Saccharide preparation | Coloration degree (480 nm) | Judgement |
|---|---|---|
| P I | 0.027 | Present invention |
| P II | 0.018 | Present invention |
| P III | 0.012 | Present invention |
| P IV | 0.016 | Present invention |
| P V | 0.015 | Present invention |
| Maltotriose | 0.623 | Control |
| Maltotetraose | 0.475 | Control |
| Maltopentaose | 0.369 | Control |
| Maltohexaose | 0.318 | Control |
| Maltoheptaose | 0.271 | Control |

As is evident from the results in Table 4, it was revealed that the newly formed non-reducing saccharides P I, P II, P III, P IV and P V only showed a slight coloration caused by the maillard reaction, i.e. the coloration degree was only 3–6% of those of their corresponding material maltooligosaccharides. The results revealed that the non-reducing saccharides formed by the present enzyme are substantially free from the maillard reaction.

EXPERIMENT 6
Enzymatic hydrolysis by glucoamylase

Fifty mg aliquots of non-reducing saccharide preparations P I, P II, P III, P IV and P V in Experiment 4 were respectively dissolved in one ml of 50 mM acetate buffer (pH 4.5), admixed with one unit of glucoamylase commercialized by Seikagaku-Kogyo Co., Ltd., Tokyo, Japan, to effect enzymatic hydrolysis at 40° C. for 6 hours. HPLC analysis only detected glucose and trehalose in all resultant mixtures. The percentages and the molecular ratios of glucose to trehalose in each saccharide are in Table 5.

TABLE 5

| Saccharide preparation | Glucose (%) | Trehalose (%) | Molecular ratio (Glucose/Trehalose) |
|---|---|---|---|
| P I | 36.2 | 63.8 | 1.07 |
| P II | 52.0 | 48.0 | 2.06 |
| P III | 61.4 | 38.6 | 3.02 |
| P IV | 68.3 | 31.7 | 4.09 |
| P V | 72.9 | 27.1 | 5.11 |

As is evident from the results in Table 5, it was revealed that (i) the non-reducing saccharide P I was hydrolyzed into one glucose molecule and one trehalose molecule; P II, hydrolyzed into 2 glucose molecules and one trehalose molecule; (iii) P III, hydrolyzed into 3 glucose molecules and one trehalose molecule; (iv) P IV, hydrolyzed into 4 glucose molecules and one trehalose molecule; and (v) P V, hydrolyzed into 5 glucose molecules and one trehalose molecule.

In view of the enzymatic reaction mechanism of glucoamylase, it was revealed that these non-reducing saccharides have a structure of saccharide consisting of one or more glucose molecules bound to one trehalose molecule via the $\alpha$-1,4 linkage or $\alpha$-1,6 linkage: The non-reducing saccharide P I is a non-reducing saccharide which has a glucose polymerization degree of 3 (DP 3) and consists of one glucose molecule bound to one trehalose molecule; P II, a non-reducing saccharide which has DP 4 and consists of 2 glucose molecules bound to one trehalose molecule; P III, a non-reducing saccharide which has DP 5 and consists of 3 glucose molecules bound to one trehalose molecule; P IV, a non-reducing saccharide which has DP 6 and consists of 4 glucose molecules bound to one trehalose molecule; and P V, a non-reducing saccharide which has DP 7 and consists of 5 glucose molecules bound to one trehalose molecule. It was revealed that, when $\beta$-amylase was act on these non-reducing saccharides similarly as in glucoamylase, P I and P II were not hydrolyzed but P III, P IV and P V were respectively hydrolyzed into one maltose molecule and one P I molecule, one maltose molecule and one P II molecule, and 2 maltose molecules and one P I molecule.

Based on these results, it was concluded that the enzymatic reaction mechanism of the present non-reducing saccharide-forming enzymes is an intramolecular conversion reaction without changing the molecular weights of substrates, i.e. an intramolecular conversion reaction without changing the glucose polymerization degrees of substrates. It was also concluded that the non-reducing saccharides P I, P II, P III, P IV and P V were respectively $\alpha$-glycosyltrehaloses ($G_n$-T, wherein the symbol "G" means glucose residue; the symbol "n", one or more integers; and the symbol "T", $\alpha,\alpha$-trehalose residue) of $\alpha$-glucosyltrehalose, $\alpha$-maltosyltrehalose, $\alpha$-maltotriosyltrehalose, $\alpha$-maltotetraosyltrehalose and $\alpha$-maltopentaosyltrehalose.

EXPERIMENT 7
Hydrolysis by enzymes

The non-reducing saccharide P I, P II, P III, P IV or P V in Experiment 4 as a substrate was subjected to an $\alpha$-amylase specimen derived from pig pancreas, an $\alpha$-glucosidase specimen derived from rice or a rat intestinal acetone powder, all of which are commercialized by Sigma Chemical Company, St. Louis, USA, and each resultant hydrolysate was analyzed for saccharide composition on HPLC. The enzymatic reaction with the $\alpha$-amylase was as follows: Dissolve 10 mg of a substrate in one ml of 50 mM phosphate buffer (pH 6.9), mix the resultant solution with one unit of the α-amylase, and incubate the resultant mixture at 37° C. for 18 hours. The enzymatic reaction with the α-glucosidase was conducted under the same conditions as in the case of α-amylase except that 50 mM acetate buffer (pH 4.0) was used as a buffer. The enzymatic reaction using the rat intestinal acetone powder was carried out under the same conditions as in the case of α-amylase except that 50 mM maleate buffer (pH 6.0) was used as a buffer. The saccharide compositions obtained by the α-amylase, α-glucosidase and rat intestinal acetone powder are respectively in Tables 6, 7 and 8.

TABLE 6

| | Saccharide composition of hydrolysate by α-amylase | | | | |
|---|---|---|---|---|---|
| Saccharide | P I | P II | G3 | G2 | G1 |
| P I | 97.3 | 0 | 2.3 | 0.4 | 0 |
| P II | 0 | 98.8 | 0.4 | 0.8 | 0 |
| P III | 61.0 | 4.8 | 0 | 33.0 | 1.2 |
| P IV | 47.2 | 3.3 | 40.4 | 7.5 | 1.6 |
| P V | 10.2 | 44.9 | 35.3 | 8.6 | 1.0 |

Note: In the table, the symbols "G3", "G2" and "G1" mean maltotriose, maltose and glucose respectively.

TABLE 7

| | Saccharide composition of hydrolysate by α-glucosidase | | |
|---|---|---|---|
| Saccharide | Glucose (%) | Trehalose (%) | Other saccharides (%) |
| P I | 36.5 | 63.0 | 0.5 |
| P II | 52.1 | 47.6 | 0.3 |
| P III | 61.7 | 38.1 | 0.2 |
| P IV | 69.5 | 30.2 | 0.3 |
| P V | 71.4 | 28.3 | 0.3 |

TABLE 8

| | Saccharide composition of hydrolysate by rat intestinal acetone powder | | |
|---|---|---|---|
| Saccharide | Glucose (%) | Trehalose (%) | Other saccharides (%) |
| P I | 37.2 | 62.4 | 0.4 |
| P II | 52.5 | 47.1 | 0.4 |
| P III | 62.0 | 37.6 | 0.4 |
| P IV | 68.8 | 30.8 | 0.4 |
| P V | 73.4 | 26.5 | 0.1 |

As is evident from the Table 6, it was revealed that the saccharide preparations P I and P II were not substantially hydrolyzed by the α-amylase, while the saccharide preparations P III, P IV and P V were hydrolyzed by the α-amylase into lower molecular weight oligosaccharides such as P I, P II, maltotriose, maltose and glucose.

As is evident from the results in Tables 7 and 8, it was revealed that, similarly as in Experiment 6 wherein glucoamylase is used, the saccharide preparations P I, P II, P III, P IV and P V were hydrolyzed by the α-glucosidase and the rat intestinal acetone powder into glucose and trehalose.

To the resultant hydrolysate obtained by the α-glucosidase or the rat intestinal acetone powder was added one unit trehalase derived from pig kidney, a product of Sigma Chemical Company, St., Louis, USA, and the mixture was incubated at pH 5.7 and 37° C. for 18 hours, followed by analyzing the saccharide composition of the resultant mixture on HPLC revealing that trehalose, formed from the saccharide preparations P I, P II, P III, P IV and P V, was hydrolyzed by trehalase into glucose molecules.

These observations are summarized in the below:

(1) The non-reducing saccharide-forming enzyme forms α-glycosyltrehalose when allowed to act on one or more reducing partial starch hydrolysates having a glucose polymerization degree of 3 or more without changing their glucose polymerization degrees; and (2) The non-reducing saccharide P V is mainly hydrolyzed by α-amylase into the non-reducing saccharide P II and maltotriose, while the non-reducing saccharide P II is phydrolyzed by glucoamylase into one trehalose molecule and 2 glucose molecules.

Based o n these results, it was concluded that the non-reducing saccharide-forming enzyme used in the present invention is an enzyme which intramolecularly converts a reducing end unit in reducing partial starch hydrolysates into a non-r educing end unit, i.e. a trehalose residue or a trehalose structure.

EXPERIMENT 8

Acute toxicity test

By using 7-week old dd-strain mice, the non-reducing saccharide preparation p I, P II, P III, P IV or P V was orally administered to the mice for acute toxicity test. As a result, it was revealed that these saccharide preparations are relatively-low in toxicity because no mouse died even when administered with them at their highest possible doses. Though not so accurate, the values of $LD_{50}$ of these saccharide preparations were 50 g/kg or more.

EXPERIMENT 9

Production of non-reducing saccharide-forming enzyme by *Arthrobacter sp.* Q36

Similarly as in Experiment 1, a seed culture of *Arthrobacter sp.* Q36 (FERM BP-4316) was cultured in- place of *Rhizobium sp.* M-11 (FERM BP-4130) by a fermenter for about 72 hours. The enzymatic activity of a non-reducing saccharide-forming enzyme in the resultant culture was about 1.2 units/ml. Similarly as in Experiment 1, a cell suspension and a supernatant, prepared from the resultant culture, were assayed for activity revealing that they had about 0.5 units/ml and about 0.7 units/ml respectively.

EXPERIMENT 10

Purification of enzyme

By using an about 18 L of the resultant culture obtained by the method in Experiment 9, a crude non-reducing saccharide-forming enzyme was purified similarly as in Experiment 2. The results in each purification step are in Table 9.

TABLE 9

| Purification step | Enzyme* activity (unit) | Specific activity (units/mg protein) | Yield (%) |
|---|---|---|---|
| Culture | 21,600 | — | 100 |
| Supernatant after cell disruption | 17,500 | 0.14 | 81 |
| Dialyzed solution after salting out with ammonium sulfate | 15,700 | 0.41 | 73 |
| Eluate from ion-exchange column | 12,600 | 6.5 | 58 |

TABLE 9-continued

| Purification step | Enzyme* activity (unit) | Specific activity (units/mg protein) | Yield (%) |
|---|---|---|---|
| Eluate from hydrophobic column | 8,820 | 98 | 41 |
| Eluate from gel filtration column | 5,290 | 201 | 24 |

Note: The symbol "*" means a non-reducing saccharide-forming enzyme.

A purified enzyme preparation, obtained as an eluate from the gel filtration column in Table 9, was determined for purity on electrophoresis similarly as in Experiment 2 revealing that it showed a single protein band, and this meant that it was an electrophoretically homogenous enzyme with a relatively-high purity.

EXPERIMENT 11
Property of enzyme

The purified enzyme preparation obtained in Experiment 10 was determined for molecular weight on SDS-PAGE to give about 76,000–86,000 daltons. The pI of the enzyme preparation was determined on isoelectrophoresis similarly as in Experiment 3 to give a pI of about 3.6–4.6. The influence of temperature and pH on the enzyme preparation, and the thermal stability and pH stability of the preparation were studied similarly as in Experiment 3. These results on the influence of temperature and pH, thermal stability and pH stability are respectively in FIGS. 5, 6, 7 and 8.

As is evident from these FIGS., the optimum temperature of the enzyme preparation is about 40° C.; the optimum pH, about 6.5–7.0; the thermal stability, up to about 40° C.; and the pH stability, about 6.0–9.5.

EXPERIMENT 12
Preparation of non-reducing saccharide

By using the purified enzyme preparation obtained in Experiment 10, the preparation and the confirmation of the structure of non-reducing saccharides were experimented in accordance with the methods in Experiments 4 and 6. As a result, it was revealed that the enzyme preparation forms α-glycosyltrehalose when allowed to act on one or more reducing partial starch hydrolysates having a glucose polymerization degree of 3 or more.

EXPERIMENT 13
Preparation and property of non-reducing saccharide-forming enzyme by known microorganism Among known microorganisms those as listed in Table 10, which had been confirmed to produce the non-reducing saccharide-forming enzymes usable in the present invention, were cultured by a fermenter at 27° C. for 72 hours similarly as in Experiment 1 except that a microorganism of Mycobacterium smegmatis (ATCC 19420) was cultured at 37° C. Eighteen L of each resultant culture was subjected to a cell disrupter, and the resultant supernatant was salted out with ammonium sulfate, dialyzed, and subjected to an ion-exchange column to obtain a partially purified enzyme preparation, followed by studying its properties.

The results are in Table 10.

TABLE 10

| Microorganism | Enzyme activity in eluate from ion-exchange column (Unit) | Optimum temperature (°C.) | Optimum pH (°C.) | Thermal stability | pH Stability |
|---|---|---|---|---|---|
| Brevibacterium helovolum (ATCC 11822) | 2,700 | About 35 | About 6.5 | Up to about 35 | About 5.5–11.0 |
| Flavobacterium aquatile (IFO 3772) | 216 | About 35 | About 6.5–6.9 | Up to about 35 | About 6.0–9.5 |
| Micrococcus luteus (IFO 3064) | 1,730 | About 35 | About 6.4–6.8 | Up to about 35 | About 6.5–8.0 |
| Micrococcus roseus (ATCC 186) | 1,340 | About 35 | About 6.8–7.2 | Up to about 35 | About 6.0–11.0 |
| Curtobacterium citreum (IFO 15231) | 1,290 | About 30 | About 6.4–6.8 | Up to about 35 | About 6.5–7.8 |
| Mycobacterium smegmatis (ATCC 19420) | 358 | About 35 | About 6.5 | Up to about 35 | About 6.0–9.0 |
| Terrabacter tumescens (IFO 12960) | 1,050 | About 35 | About 6.5–7.0 | Up to about 35 | About 6.0–9.5 |
| Rhizobium sp. M-11 (FERM BP-4130) | 11,300 | About 40 | About 7.0 | Up to about 40 | About 6.0–9.0 |
| Arthrobacter sp. Q36 (FERM BP-4316) | 12,600 | About 40 | About 6.5–7.0 | Up to about 40 | About 6.0–9.5 |

In accordance with the method in Experiment 12, non-reducing saccharides were prepared by partially purified enzyme preparations from known microorganisms, and studied on their structures revealing that, similarly as the non-reducing saccharide-forming enzyme from *Rhizobium sp.* M-11, every enzyme preparation formed α-glycosyltrehalose when allowed to act on one or more reducing partial starch hydrolysates having a glucose polymerization degree of 3 or more.

The followings are the explanations of trehalose-releasing enzymes from *Rhizobium sp.* M-11 and *Arthrobacter sp.* Q36, as well as from known microorganisms:

EXPERIMENT 14
Production of trehalose-releasing enzyme by *Rhizobium sp.* M-11

A liquid nutrient culture medium, consisting of 42.0 w/v % "PINE-DEX #4", a partial starch hydrolysate of Matsutani Chemical Ind., Co., Ltd., Kyoto, Japan, 0.5 w/v % peptone, 0.1 w/v % yeast extract, 0.1 w/v % disodium hydrogenphosphate, 0.1 W/V % potassium hydrogenphosphate and water, was adjusted to pH 7.0. About 100 ml aliquots of the liquid nutrient culture medium were placed in 500-ml Erlenmeyer flasks, autoclaved at 120° C. for 20 min to effect sterilization, cooled, inoculated with a stock culture of *Rhizobium sp.* M-11 (FERM BP-4130), and incubated at 27° C. for 24 hours under stirring conditions of 130 rpm. The resultant cultures were pooled for a seed culture.

About 20 L of a fresh preparation of the same liquid nutrient culture medium as used in the above culture was placed in a 30-L fermenter, sterilized, cooled to 27° C., inoculated with one w/v % of the seed culture, and incubated under agitation-aeration conditions at 27° C. and a pH of 6.0–8.0 for about 72 hours.

The activities of a non-reducing saccharide-forming enzyme and a trehalose-releasing enzyme accumulated in the culture were respectively about 1.5 units/ml and about 2 units/ml. A portion of the culture was centrifuged into cells and a culture supernatant, and the cells were suspended in 50 mM phosphate buffer (pH 7.0) to give the same volume of the portion, followed by assaying the enzyme activities of the cell suspension and the culture supernatant. The activities of the non-reducing saccharide-forming enzyme and the trehalose-releasing enzyme in the cell suspension were respectively about 0.6 units/ml and about 0.8 units/ml, and the culture supernatant contained about 0.9 units/ml of the non-reducing saccharide-forming enzyme and about 1.2 units/ml of the trehalose-releasing enzyme.

EXPERIMENT 15
Purification of enzyme

An about 18 L of a culture obtained by the method in Experiment 14 was treated to disrupt cells with "MINI-RABO", a supper high-pressure cell disrupter commercialized by Dainippon Pharmaceutical Co., Ltd., Tokyo, Japan. The resultant suspension was centrifuged at 10,000 rpm for 30 min to obtain an about 16 L supernatant. Ammonium sulfate was added to and dissolved in the supernatant to give a saturation degree of 0.2, and the resultant solution was allowed to stand at 4° C. for one hour and centrifuged at 10,000 rpm for 30 min to obtain a supernatant.

Ammonium sulfate was added to and dissolved in the resultant supernatant to give a saturation degree of 0.6, and the resultant solution was allowed to stand at 4° C. for 24 hours and centrifuged, followed by collecting a precipitate and dissolving it in 10 mM phosphate buffer (pH 7.0). The solution thus obtained was dialyzed against a fresh preparation of the same phosphate buffer for 24 hours, and centrifuged to remove insoluble substances. Three hundred and sixty ml of the dialyzed solution was divided into 2 portions which were then separately subjected to column chromatography using a column packed with 300 ml of "DEAE-TOYOPEARL®", an ion-exchanger commercialized by Tosoh Corporation, Tokyo, Japan.

Figure 9:
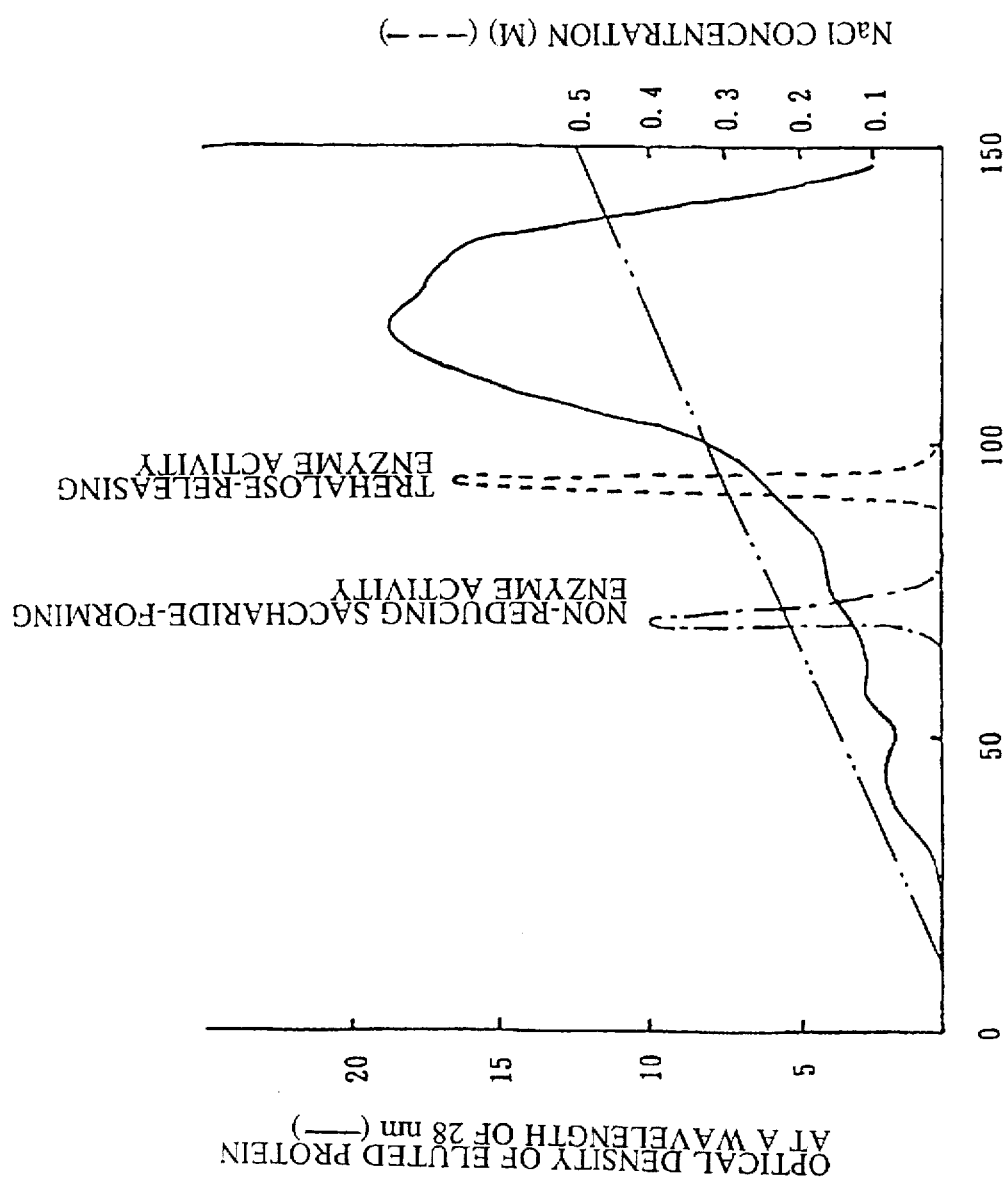
FIG. 9 shows the elution patterns of a trehalose-releasing enzyme and a non-reducing saccharide-forming enzyme usable in the present invention on column chromatography using "TOYOPEARL".

The objective non-reducing saccharide-forming enzyme and trehalose-releasing enzyme were adsorbed on the ion-exchanger, and eluted separately from the column with a fresh preparation of the same phosphate buffer supplemented with salt at different salt concentrations. The elution pattern from the column or the column chromatogram is in FIG. 9. The non-reducing saccharide-forming enzyme was eluted from the column at a salt concentration of about 0.2 M, while the trehalose-releasing enzyme was eluted from the column at a salt concentration of about 0.3 M. The fractions containing either of the objective enzymes were separately pooled and purified as follows:

The pooled fractions containing the non-reducing saccharide-forming enzyme were dialyzed against a fresh preparation of the same phosphate buffer supplemented with 2M ammonium sulfate. The dialyzed solution was centrifuged to remove insoluble substances, and the resultant supernatant was subjected to hydrophobic column chromatography using a column packed with 300 ml of "BUTYL-TOYOPEARL® 650", a hydrophobic gel commercialized by Tosoh Corporation, Tokyo, Japan. The enzyme adsorbed on the gel was eluted from the column with a liner gradient buffer ranging from 2M to 0M, followed by recovering fractions with the enzyme activity. The resultant fractions were pooled and subjected to gel filtration chromatography using a column packed with 300 ml of "TOYOPEARL® HW-55", a resin for gel chromatography commercialized by Tosoh Corporation, Tokyo, Japan, followed by recovering fractions with the enzyme activity.

Fractions with a trehalose-releasing enzyme activity eluted from the column of "DEAE-TOYOPEARL®" were pooled and treated similarly as in the purification steps used in the preparation of the non-reducing saccharide-forming enzyme in such a manner that they were dialyzed against a buffer containing 2M ammonium sulfate, and successively subjected to hydrophobic column chromatography and gel filtration chromatography.

The total enzyme activity, specific activity and yield of the non-reducing saccharide-forming enzyme in each purification step are in Table 11, while those of the trehalose-releasing enzyme are in Table 12.

TABLE 11

| Purification step | Total enzyme* activity (units) | Specific activity (units/mg protein) | Yield (%) |
| --- | --- | --- | --- |
| Culture | 28,500 | — | 100 |
| Supernatant after cell disruption | 22,900 | 0.12 | 80 |
| Dialyzed solution after salting out | 21,100 | 0.43 | 74 |
| Eluate from ion-exchange column | 15,200 | 6.2 | 53 |
| Eluate from hydrophobic column | 7,950 | 101 | 28 |
| Eluate after gel filtration column | 5,980 | 197 | 21 |

Note: The symbol "*" means a non-reducing saccharide-forming enzyme.

TABLE 12

| Purification step | Total enzyme** activity (units) | Specific activity (units/mg protein) | Yield (%) |
| --- | --- | --- | --- |
| Culture | 37,400 | — | 100 |
| Supernatant after cell disruption | 31,500 | 0.17 | 84 |
| Dialyzed solution after salting out | 29,200 | 0.60 | 78 |
| Eluate from ion-exchange column | 25,400 | 5.3 | 68 |
| Eluate from hydrophobic column | 18,700 | 98.5 | 50 |
| Eluate from gel filtration column | 11,600 | 240 | 31 |

Note: The symbol "**" means a trehalose-releasing enzyme.

The purified enzyme preparations, obtained as an eluate from the gel filtration columns in Tables 11 and 12, were determined for purity on electrophoresis in a 7.5% polyacrylamide gel. As a result, each enzyme preparation was observed as a single protein band revealing that they were electrophoretically-homogeneous preparations with a relatively-high purity.

EXPERIMENT 16
Property of trehalose-releasing enzyme

A portion of a purified trehalose-releasing enzyme preparation, obtained by the method in Experiment 15, was electrophoresed in a 10% sodium dodecylsulfate polyacrylamide gel, and determined for molecular weight by comparing it with marker proteins commercialized by Japan Bio-Rad Laboratories, Tokyo, Japan, revealing that it has a molecular weight of about 58,000–68,000 daltons.

Another portion of the purified enzyme preparation was isoelectrophoresed in a polyacrylamide gel, and the resultant gel was sliced into pieces which were then measured for pH revealing that the enzyme has a pI of about 3.3–4.3.

Figure 10:
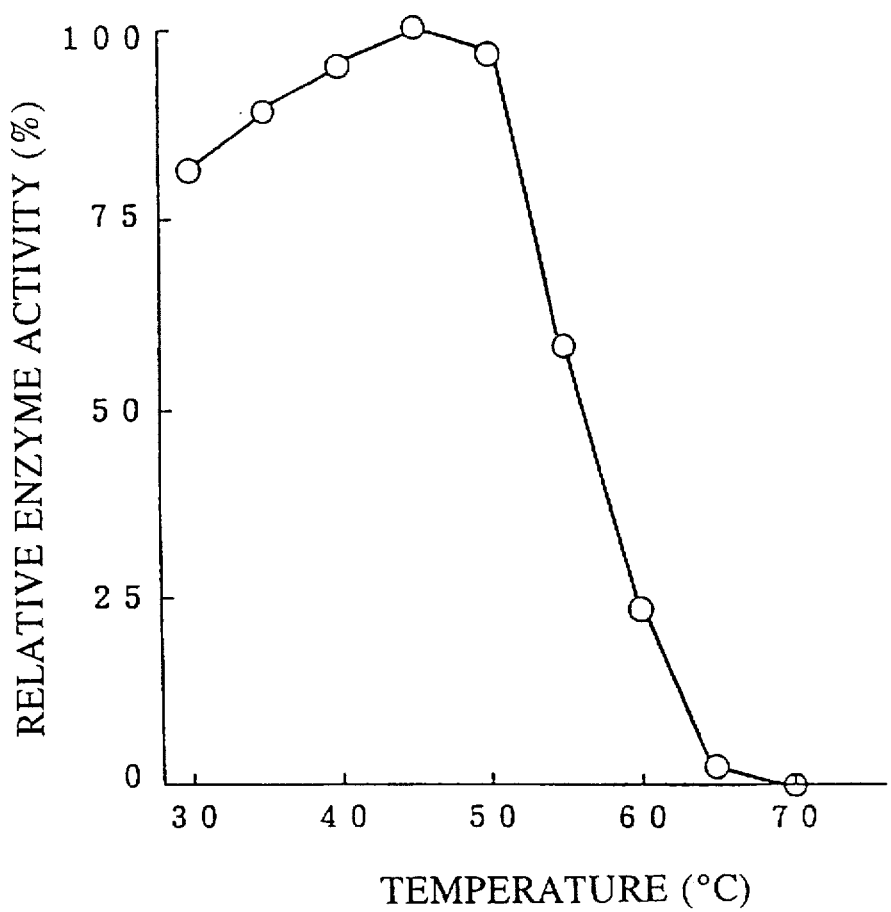
FIG. 10 shows the influence of temperature on a trehalose-releasing enzyme derived from *Rhizobium sp.* M-11.
Figure 11:
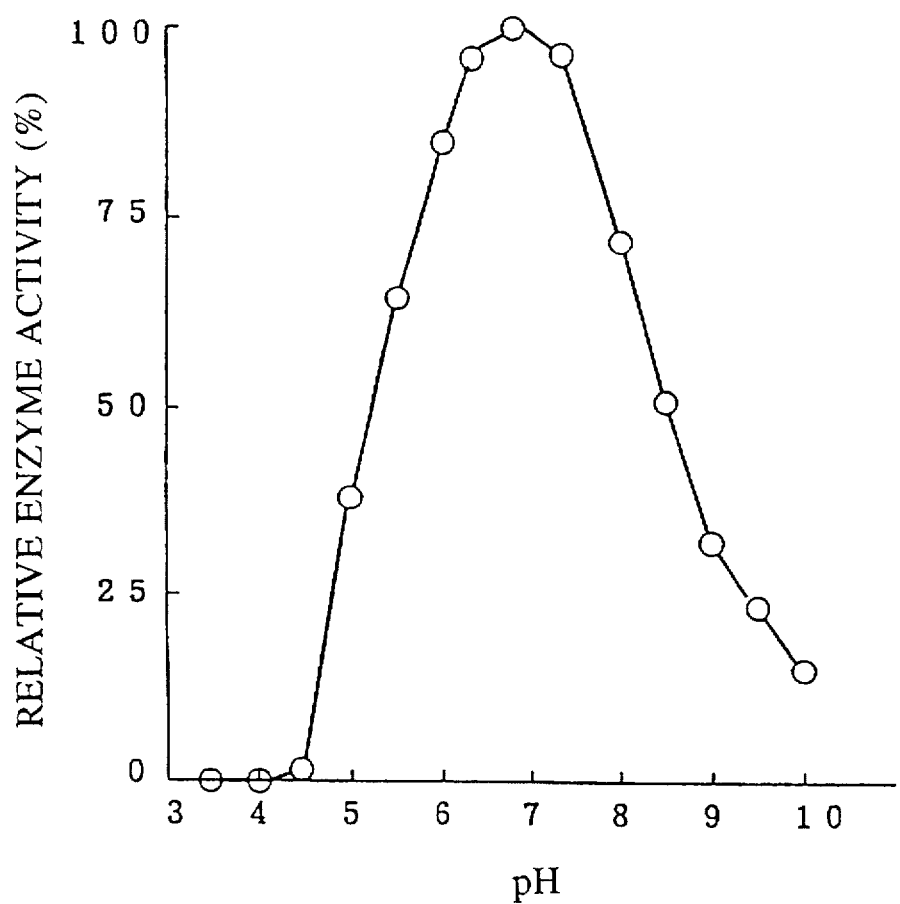
FIG. 11 shows the influence of pH on a non-reducing saccharide-forming enzyme derived from *Rhizobium sp.* M-11.
Figure 12:
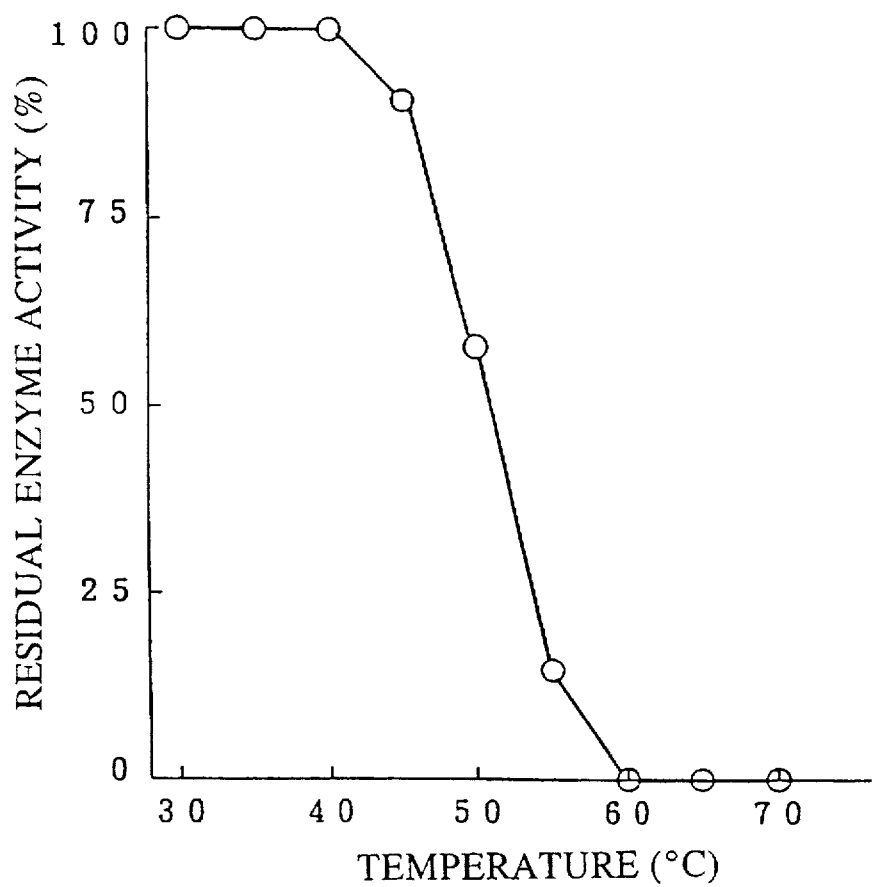
FIG. 12 shows the influence of temperature on the stability of a trehalose-releasing enzyme derived from *Rhizobium sp.* M-11.
Figure 13:
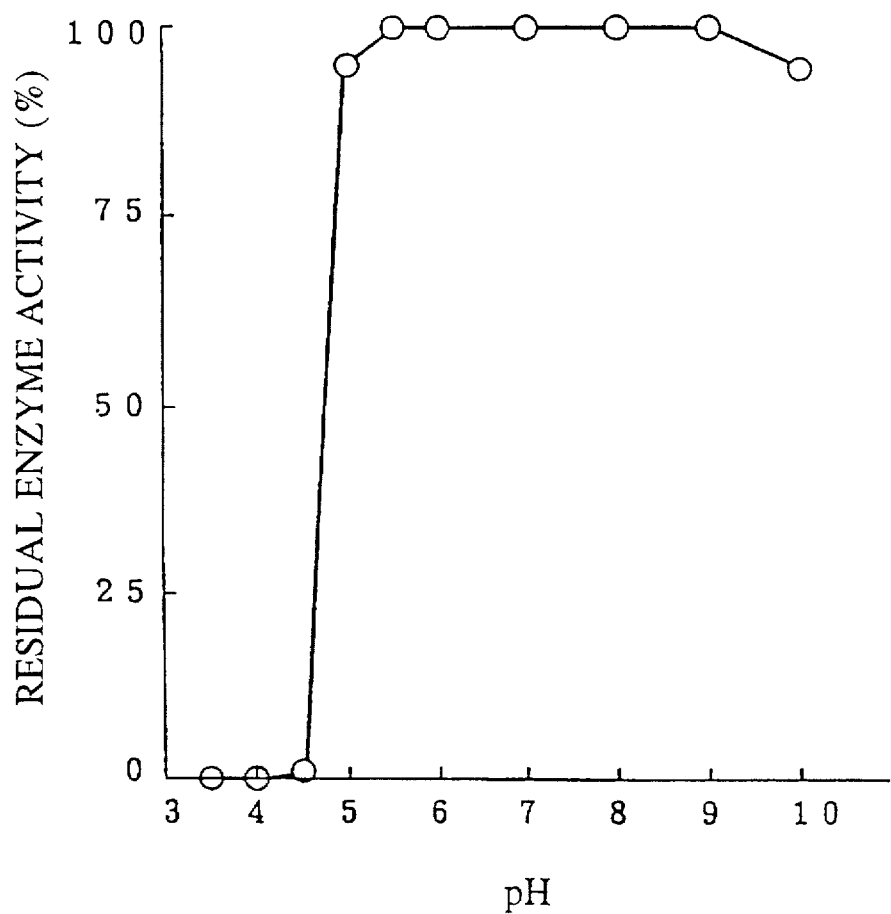
FIG. 13 shows the influence of pH on the stability of a trehalose-releasing enzyme derived from *Rhizobium sp.* M-11.
Figure 14:
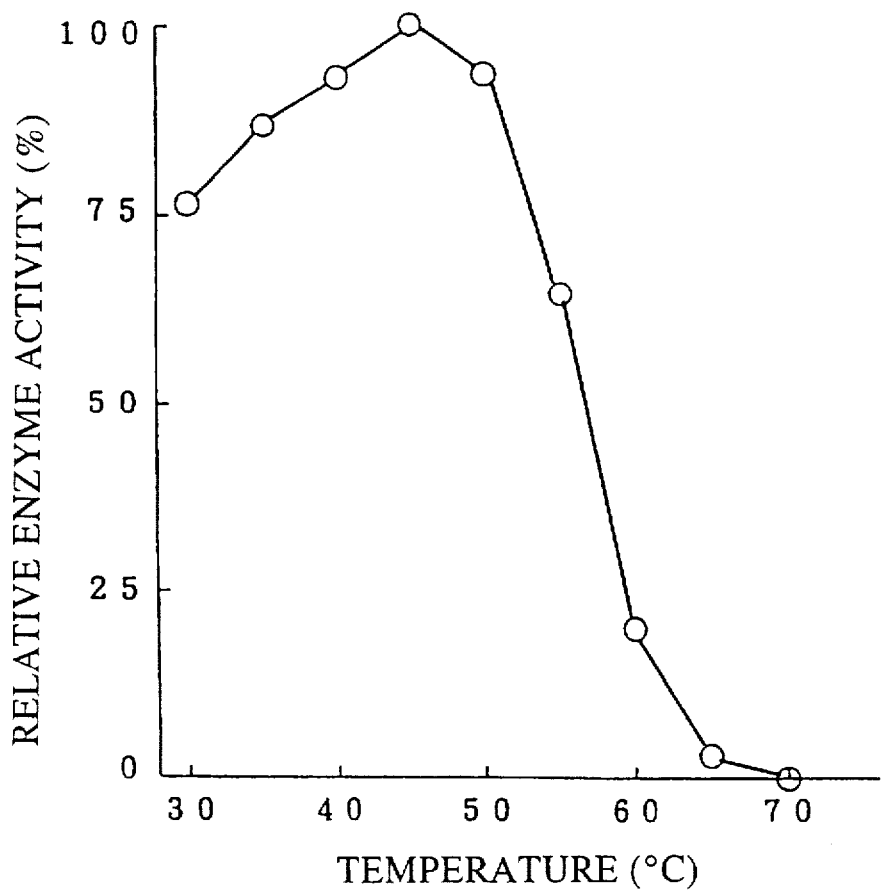
FIG. 14 shows the influence of temperature on the activity of a trehalose-releasing enzyme derived from *Arthrobacter sp.* Q36.
Figure 15:
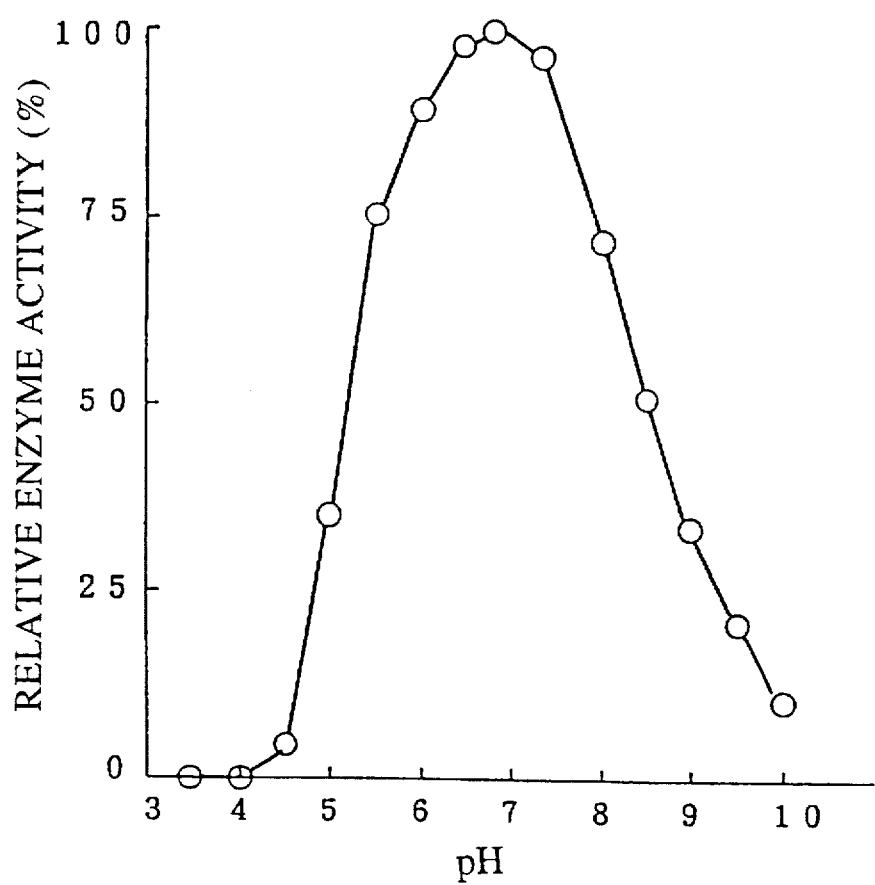
FIG. 15 shows the influence of pH on the activity of a trehalose-releasing enzyme derived from *Arthrobacter sp.* Q36.
Figure 16:
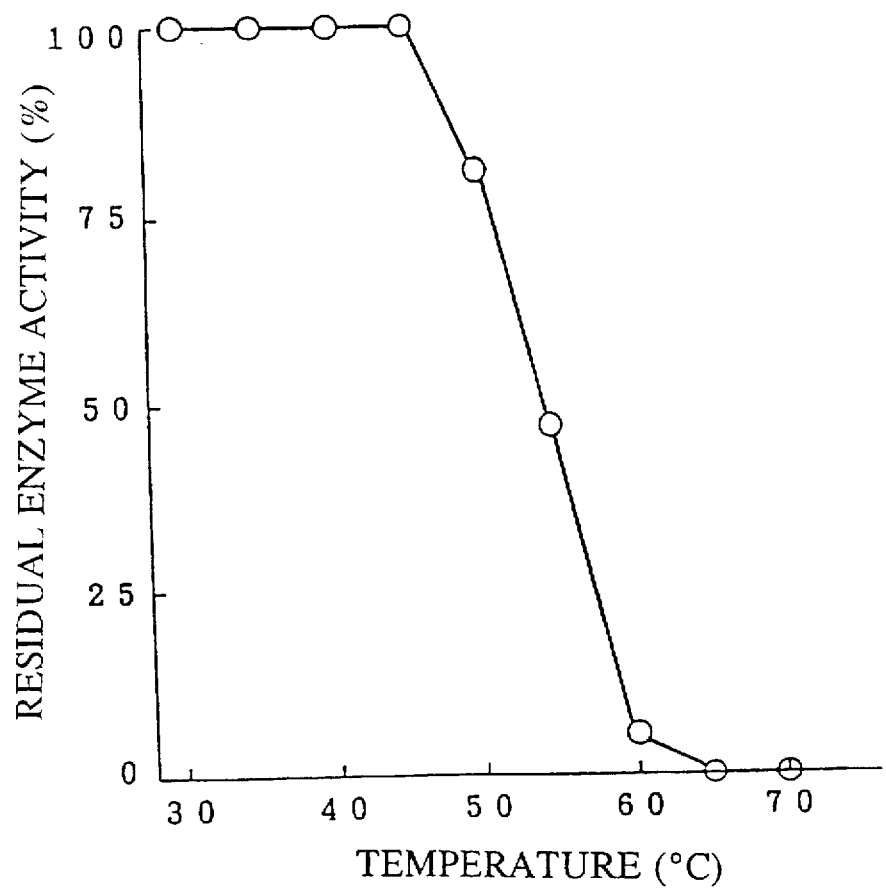
FIG. 16 shows the influence of temperature on the activity of a trehalose-releasing enzyme derived from *Arthrobacter sp.* Q36.
Figure 17:
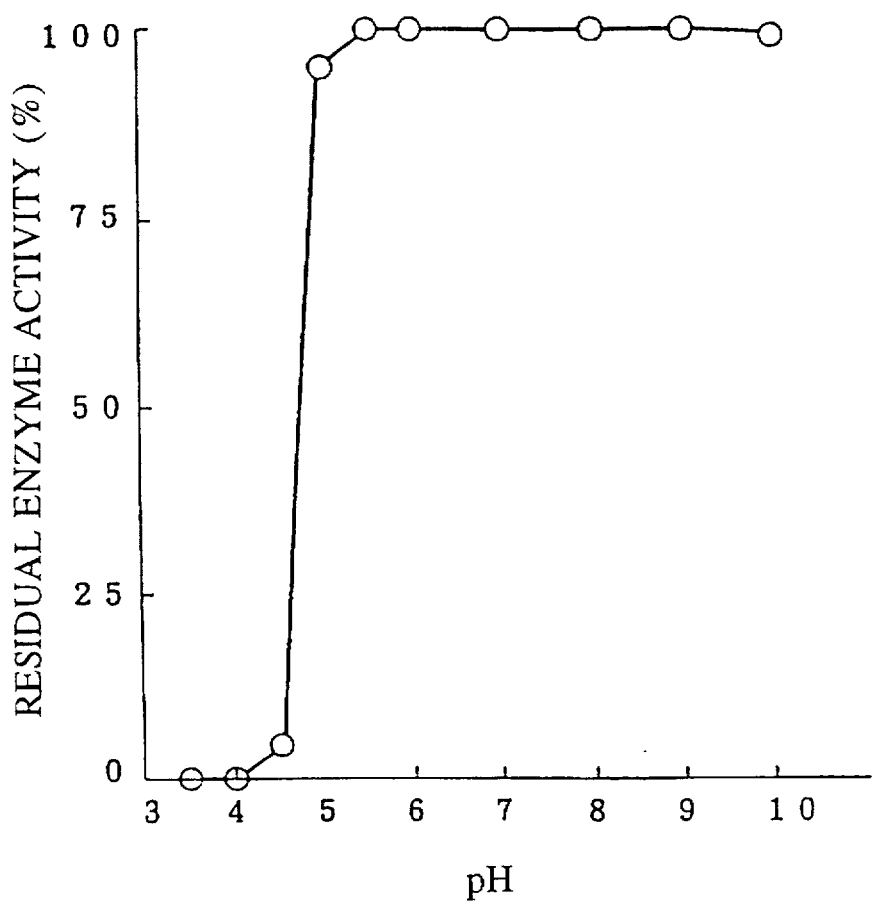
FIG. 17 shows the influence of pH on the activity of a trehalose-releasing enzyme derived from *Arthrobacter sp.* Q36.

The influences of temperature and pH on the enzyme activity were studied in accordance with the assay for enzyme activity. These results were respectively in FIG. 10 (effect of temperature) and FIG. 11 (effect of pH). The optimum temperature of the enzyme was about 45° C. when incubated at pH 7.0 for 30 min, and the optimum pH was about 6.0–7.5 when incubated at 40° C. for 30 min. The thermal stability of the enzyme was determined by incubating it in 50 mM phosphate buffers (pH 7.0) for 60 min at different temperatures, cooling the buffers in test tubes with cold water, and assaying the remaining enzyme activity in each buffer. The pH stability of the enzyme was determined by incubating it in 50 mM phosphate buffers having different pHs at 25° C. for 16 hours, adjusting the buffers to pH 7, and assaying the remaining enzyme activity in each buffer. The results of the thermal- and pH-stabilities of the enzyme were respectively in FIGS. 12 and 13 revealing that the enzyme was stable up to a temperature of about 40° C. and stable at a pH in the range of about 5–10.

EXPERIMENT 17

Preparation of trehalose by α-glycosyltrehalose

α-Glycosyltrehalose as a substrate was prepared in accordance with the method in Experiment 4: To a 20% aqueous solution of a reducing partial starch hydrolysate selected from maltotriose, maltotetraose, maltopentaose, maltohexaose and maltoheptaose was added 2 units/g substrate, d.s.b., of a purified non-reducing saccharide-forming enzyme obtained by the method in Experiment 15, subjected to an enzymatic reaction at 40° C. and pH 7.0 for 48 hours. The reaction mixture was heated to inactivate the remaining enzyme, filtered, decolored, desalted and concentrated into a high saccharide content solution which was then column chromatographed by using XT-1016 in Na⁺-form, an ion-exchanger commercialized by Tokyo Organic Chemical Industries, Ltd., Tokyo, Japan. In the column chromatography, the ion-exchanger was packed in 3-jacketed stainless steel columns, having an inner diameter of 2.0 cm and a length of one m each, which were then cascaded in series, heated to give the inner column temperature of 55° C., applied with 5 v/v % of the concentrated saccharide solution to the resin while keeping at 55° C., and fed with 55° C. hot water at SV 0.13 to obtain high-purity non-reducing saccharides having a trehalose structure as an end unit and a glucose polymerization degree of 3 or more. Among the resultant high-purity preparations, the purities of the preparations of glucosyltrehalose, maltotriosyltrehalose, maltotriosyltrehalose, maltotetraosyltrehalose and maltopentaosyltrehalose were respectively 97.6%, 98.6%, 99.6%, 98.3% and 98.1%, d.s.b.

An aqueous solution containing 20%, d.s.b., of one of the above 5 non-reducing saccharide preparations, namely α-glycosyltrehalose preparations, was prepared, followed by mixing it with 2 units/g substrate, d.s.b., of the purified trehalose-releasing enzyme obtained in Experiment 15, and subjecting the resultant to an enzymatic reaction at 40° C. and pH 7.0 for 48 hours. The resultant each reaction mixture was desalted, and analyzed for saccharide composition on HPLC using "WAKOBEADS WB-T-330 column", a column of Wako Pure Chemical Industries Ltd., Tokyo, Japan. As a control, a fresh preparation of the same trehalose-releasing enzyme was allowed to act on maltotriose, maltotetraose, maltopentaose, maltohexaose or maltoheptaose, and the resultant each reaction mixture was analyzed for saccharide composition on HPLC. The results are in Table 13.

TABLE 13

| Substrate | Product | Elution time on HPLC (min) | Percentage (%) |
|---|---|---|---|
| Glucosyltrehalose | Trehalose | 27.4 | 17.5 |
|  | Glucose | 33.8 | 6.5 |
|  | Glucosyltrehalose | 23.3 | 76.0 |
| Maltosyltrehalose | Trehalose | 27.4 | 44.3 |
|  | Maltose | 28.7 | 44.4 |
|  | Maltosyltrehalose | 21.6 | 11.3 |
| Maltotriosyltrehalose | Trehalose | 27.4 | 39.5 |
|  | Maltotriose | 25.9 | 60.0 |
|  | Maltotriosyltrehalose | 19.7 | 0.5 |
| Maltotetraosyltrehalose | Trehalose | 27.4 | 34.2 |
|  | Maltotetraose | 24.1 | 65.5 |
|  | Maltotetraosyltrehalose | 18.7 | 0.3 |
| Maltopentaosyltrehalose | Trehalose | 27.4 | 29.1 |
|  | Maltopentaose | 22.6 | 70.6 |
|  | Maltopentaosyltrehalose | 17.8 | 0.3 |
| Maltotriose | Maltotriose | 25.9 | 100 |
| Maltotetraose | Maltotetraose | 24.1 | 100 |
| Maltopentaose | Maltopentaose | 22.6 | 100 |
| Maltohexaose | Maltohexaose | 21.8 | 100 |
| Maltoheptaose | Maltoheptaose | 21.0 | 100 |

The results in Table 13 clearly show that:

1. The trehalose-releasing enzyme specifically hydrolyzes the linkage between a trehalose moiety and a glycosyl moiety in α-glycosyltrehalose to form trehalose and a reducing saccharide having a glucose polymerization degree of one or more; and
2. Maltooligosaccharide is not hydrolyzed by the trehalose-releasing enzyme.

These results confirm that the trehalose-releasing enzyme usable in the present invention is an enzyme which has a new reaction mechanism of specifically hydrolyzing the linkage between a trehalose moiety and other glycosyl moiety in α-glycosyltrehalose to release trehalose.

To purify trehalose in each reaction mixture, it was subjected to column chromatography using a column packed with "XT-1016", a strong-acid cation exchange resin in Na⁺-form commercialized by Tokyo Organic Chemical Industries, Ltd., Tokyo, Japan, followed by recovering fractions containing 97% or more of trehalose. The fractions were pooled and concentrated into an about 65% solution which was then allowed to stand at 25° C. for 2 days to crystallize trehalose into hydrous crystalline trehalose, followed by separating and drying it in vacuo to obtain a high-purity trehalose preparation with a purity of 99% or more, d.s.b. The yields of trehalose from glucosyltrehalose, maltosyltrehalose, maltotriosyltrehalose, maltotetraosyltrehalose and maltopentaosyltrehalose used as a substrate were respectively 9.5%, 14.9%, 16.0%, 18.5% and 17.7%, d.s.b. The high-purity trehalose preparations and a commercially available trehalose specimen as a standard were studied for melting point, heat of fusion, specific rotation, infrared absorption spectrum, powdery X-ray diffraction pattern, and readiness of hydrolysis by a trehalase specimen derived from pig kidney, commercialized by Sigma Chemical Co., St. Louise, USA. As a result, every trehalose preparation showed a melting point of 97.0°±0.5° C., a heat of fusion of 57.8±1.2 kJ/mole and a specific rotation of +182°1.1°, and these values well corresponded with those of the standard trehalose specimen, and the infrared absorption spectra and powdery X-ray diffraction patterns of the trehalose preparations also well corresponded with those of the standard trehalose specimen. Similarly as the standard trehalose specimen, the trehalose preparations were decomposed into glucose molecules. As is evident from these results, it was identified that the saccharide, which is formed by allowing the trehalose-releasing enzyme to act on α-glycosyltrehalose, is trehalose.

EXPERIMENT 18

Preparation of trehalose from reducing partial starch hydrolysates

A suspension containing 5% waxy corn starch was gelatinized by heating, adjusted to pH 4.5, heated to 50° C., mixed with 4,000 units/g starch, d.s.b., of an isoamylase specimen commercialized by Hayashibara Biochemical Laboratories Inc., Okayama, Japan, and subjected to an enzymatic reaction for 20 hours. The reaction mixture was autoclaved at 120° C. for 10 min, cooled to 60° C., and subjected to gel filtration column chromatography using a column packed with 750 ml of "TOYOPEARL® HW-50S", a gel product commercialized by Tosoh Corporation, Tokyo, Japan, to obtain reducing partial starch hydrolysates having a glucose polymerization degree of 35–10.

Either of the resultant reducing partial starch hydrolysates or maltotriose having a glucose polymerization degree of 3, as a substrate, was dissolved in 10 mM phosphate buffer (pH 7.0) into a one % solution which was then mixed with a purified non-reducing saccharide-forming enzyme and a purified trehalose-releasing enzyme, which were prepared by the method in Experiment 15, in respective amounts of 4 units/g substrate, d.s.b., and subjected to an enzymatic reaction at 40° C. for 24 hours. After completion of the reaction, a portion of the resultant reaction mixture was desalted and analyzed on HPLC.

The rest of the reaction mixture was heated to 50° C., adjusted to pH 4.5, admixed with 50 units/g substrate, d.s.b., of glucoamylase commercialized by Seikagaku-Kogyo Co., Ltd., Tokyo, Japan, and subjected to an enzymatic reaction for 24 hours. Similarly as above, a portion of the resultant reaction mixture was desalted and analyzed on HPLC. The results are in Table 14.

TABLE 14

| Glucose polymerization degree of reducing partial starch hydro- lysate | Reaction product | Composition (%) A | B |
|---|---|---|---|
| 34.1 | Trehalose | 80.8 | 83.5 |
|  | Glucose | 0.2 | 16.5 |
|  | Reducing oligosaccharides | 14.4 | 0.0 |
|  | Glucosyltrehalose | 4.6 | 0.0 |
| 26.2 | Trehalose | 79.7 | 82.5 |
|  | Glucose | 0.2 | 17.5 |
|  | Reducing oligosaccharides | 15.3 | 0.0 |
|  | Glucosyltrehalose | 4.8 | 0.0 |
| 18.1 | Trehalose | 77.7 | 80.7 |
|  | Glucose | 0.2 | 19.3 |
|  | Reducing oligosaccharides | 17.0 | 0.0 |
|  | Glucosyltrehalose | 5.1 | 0.0 |
| 15.2 | Trehalose | 75.0 | 78.5 |
|  | Glucose | 0.3 | 21.5 |
|  | Reducing oligosaccharides | 18.6 | 0.0 |
|  | Glucosyltrehalose | 6.1 | 0.0 |
| 10.0 | Trehalose | 66.1 | 70.1 |
|  | Glucose | 0.3 | 29.9 |
|  | Reducing oligosaccharides | 27.6 | 0.0 |
|  | Glucosyltrehalose | 7.7 | 0.0 |

TABLE 14-continued

| Glucose polymerization degree of reducing partial starch hydro- lysate | Reaction product | Composition (%) A | B |
|---|---|---|---|
| 3 | Trehalose | 4.2 | 20.8 |
| (Maltotriose) | Glucose | 2.1 | 79.2 |
|  | Maltotriose | 65.0 | 0.0 |
|  | Glucosyltrehalose | 28.7 | 0.0 |

Note : In the Table, the symbol "A" means a composition after enzymatic reaction of a non-reducing saccharide-forming enzyme and a trehalose-releasing enzyme, and the symbol "B" means a composition after enzymatic reaction of glucoamylase. The wording "Glucosyltrehalose" means a non-reducing saccharide having a trehalose structure as an end unit and a glucose polymerization degree of 3 or more.

As is shown in Table 14, in the case of using as a substrate maltotriose having a glucose polymerization degree of 3, the trehalose yield after the enzymatic reactions of the non-reducing saccharide-forming enzyme and the trehalose-releasing enzyme was as low as 4.2%, while in the case of using as a substrate partial starch hydrolysates having a glucose polymerization degree of 10–34.1, the trehalose yield was high, i.e. 66.1–80.8%. It was found that the higher the glucose polymerization degree of the reducing partial starch hydrolysates as a substrate, the higher the purity of trehalose in the resultant reaction mixtures. It was also found that the purity of trehalose in the resultant reaction mixture can be more increased by allowing glucoamylase to act on the reaction mixtures, which were prepared by these enzymes, to hydrolyze the remaining non-reducing saccharides, having a trehalose structure as an end unit and a glucose polymerization degree of 3 or more, into trehalose and glucose molecules.

EXPERIMENT 19

Maillard reaction

A solution, containing one % of glycine, 10% of a high-purity trehalose preparation with a purity of 99.5%, d.s.b., obtained by the method in Experiment 17, and 50 mM phosphate buffer (pH 7.0), was kept at 100° C. for 90 min, followed by cooling the resultant solution and determining the absorbance at a wave length of 480 nm in a 1-cm cell. As a control, glucose and maltose were similarly treated as above, and the resultants were determined for absorbance at a wave length of 480 nm. The results are in Table 15.

TABLE 15

| Saccharide preparation | Coloration degree (480 nm) |
|---|---|
| Trehalose (Present invention) | 0.006 |
| Glucose (Control) | 1.671 |
| Maltose (Control) | 0.926 |

As is evident from the results in Table 15, it was revealed that the trehalose preparation was slightly colored on the maillard reaction, i.e. the coloration degree was only about 0.4–0.6% of that of glucose or maltose. The results show that the present trehalose preparation is substantially free from the maillard reaction. Thus, the preparation is a saccharide which does not substantially deteriorate amino acids even when mixed with them.

EXPERIMENT 20

Utilization test in vivo

In accordance with the method as reported by H. Atsuji et al. in "Rinsho-Eiyo", Vol.41, No.2, pp.200–208 (1972), 30 g of a high-purity trehalose preparation with a purity of 99.5%, d.s.b., obtained by the method in Experiment 17 was dissolved in water into a 20 w/v % aqueous solution which was then orally administered to 6 healthy male volunteers, 26-, 27-, 28-, 29-, 30- and 31-year-old. The volunteers were collected their blood at a prescribed time interval, and each collected blood was assayed for blood sugar-and insulin-levels. As a control glucose was used. As a result, the trehalose preparation showed the same dynamics as glucose, i.e. the blood sugar- and insulin-levels showed their maxima at an about 0.5–1 hour after their administrations. It was revealed that the trehalose preparation is readily assimilated, absorbed, metabolized and utilized by the body as an energy source.

EXPERIMENT 21
Acute toxicity test

By using mice, a powdery saccharide composition with a reduced reducibility, obtained by the method in EXample A-5, A-7 or A-8, was orally administered to the mice for acute toxicity test. As a result, it was revealed that these powdery saccharide compositions have a relatively-low toxicity and no mouse died even when administered with their highest possible doses. Though not so accurate, the $LD_{50}$ of them is 50 g/kg or more.

EXPERIMENT 22
Production of trehalose-releasing enzyme by *Arthrobacter sp.* Q36

Similarly as in Experiment 14, a seed culture of *Arthrobacter sp.* Q36 (FERM BP-4316) was cultured by a fermenter for about 72 hours in place of *Rhizobium sp.* M-11 (FERM BP-4130). The activities of a non-reducing saccharide-forming enzyme and a trehalose-releasing enzyme in the resultant culture were respectively about 1.3 units/ml and about 1.8 units/ml. Similarly as in Experiment 14, a cell suspension and a culture supernatant, prepared from the resultant culture, were assayed revealing that the former had about 0.5 units/ml of the non-reducing saccharide-forming enzyme and about 0.5 units/ml of the trehalose-releasing enzyme, and that the latter had about 0.8 units/ml of the non-reducing saccharide-forming enzyme and about 1.3 units/ml of the trehalose-releasing enzyme.

EXPERIMENT 23
Purification of enzyme

By using an about 18 L of a culture containing enzymes obtained by the method in Experiment 22, purified enzyme preparations were obtained similarly as the method in Experiment 15. The results in each purification step for a non-reducing saccharide-forming enzyme and a trehalose-releasing enzyme are respectively in Tables 16 and 17.

TABLE 16

| Purification step | Enzyme* activity (unit) | Specific activity (units/mg protein) | Yield (%) |
|---|---|---|---|
| Culture | 23,700 | — | 100 |
| Supernatant after cell disruption | 22,400 | 0.15 | 95 |
| Dialyzed solution after salting out with ammonium sulfate | 20,200 | 0.51 | 85 |
| Eluate from ion-exchange column | 15,100 | 6.5 | 64 |

TABLE 16-continued

| Purification step | Enzyme* activity (unit) | Specific activity (units/mg protein) | Yield (%) |
|---|---|---|---|
| Eluate from hydrophobic column | 8,450 | 115 | 36 |
| Eluate from gel filtration column | 6,120 | 217 | 26 |

Note: The symbol "*" means a non-reducing saccharide-forming enzyme.

TABLE 17

| Purification step | Enzyme** activity | Specific activity (unit) | Yield (%) (units/mg protein) |
|---|---|---|---|
| Culture | 32,500 | — | 100 |
| Supernatant after cell disruption | 30,100 | 0.19 | 93 |
| Dialyzed solution after salting out with ammonium sulfate | 25,400 | 0.72 | 78 |
| Eluate from ion-exchange column | 22,700 | 22.3 | 70 |
| Eluate from hydrophobic column | 15,200 | 215 | 47 |
| Eluate from gel filtration column | 11,600 | 497 | 36 |

Note: The symbol "**" means a trehalose-releasing enzyme.

Purified enzyme preparations of the non-reducing saccharide-forming enzyme and the trehalose-releasing enzyme, obtained as the eluates from gel filtration columns in Tables 16 and 17, were determined for purity on electrophoresis similarly as in Experiment 15. As a result, they were respectively found as a single band revealing that they were electrophoretically homogenous and relatively-high in purity.

EXPERIMENT 24
Property of enzyme

A purified trehalose-releasing enzyme preparation, obtained by the method in Experiment 23, was determined for molecular weight on SDS-PAGE to give about 57,000–67,000 daltons. The pI of the enzyme preparation was determined on isoelectrophoresis similarly as in Experiment 3 revealing that it is about 3.6–4.6. The influences of temperature and pH on the enzyme activity, as well as the thermal stability and pH stability, were studied similarly as in Experiment 16. The results of them are respectively in FIGS. 14–17.

As is evident from these Figures, the optimum temperature of the enzyme preparation is about 45° C.; the optimum pH, about 6.0–7.5; the thermal stability, up to a temperature of about 45° C.; and the pH stability, about 5.0–10.0.

EXPERIMENT 25

Preparation of trehalose from α-glycosyltrehalose By using a purified enzyme preparation obtained by the method in Experiment 23, trehalose was prepared from non-reducing saccharides having a trehalose structure as an end unit and a glucose polymerization degree of 3 or more according to the method in Experiment 17 revealing that the enzyme preparation releases trehalose from α-glycosyltrehalose similarly as the trehalose-releasing enzyme derived from *Rhizobium sp.* M-11.

EXPERIMENT 26
Production and property of trehalose-releasing enzyme by known microorganism Among known microorganisms, those of the species Brevibacterium helvolum (ATCC 11822) and Micrococcus roseus (ATCC 186), which had been confirmed by the present inventors to produce the trehalose-releasing enzymes usable in the present invention, were respectively cultured by a fermenter at 27° C. for 72 hours similarly as in Experiment 14. About 18 L of each resultant culture was similarly as in Experiment 15 subjected to a cell disrupter and centrifuged to obtain a supernatant which was then successively salted out with ammonium sulfate, dialyzed and subjected to an ion-exchange column to obtain a partially purified enzyme preparation, followed by studying the properties. The results are in Table 18 including those of *Rhizobium sp.* M-11 and *Arthrobacter sp.* Q36.

TABLE 18

| Microorganism | Enzyme activity of eluate from ion-exchange column (unit) | Optimum temperature (°C.) | Optimum pH | Thermal stability (°C.) | pH Stability |
|---|---|---|---|---|---|
| Brevibacterium helvolum (ATCC 11822) | 6,070 | About 40 | About 6.5–6.8 | Up to about 40 | About 5.5–9.5 |
| Micrococcus roseus (ATCC 186) | 3,010 | About 35 | About 6.8 | Up to about 30 | About 6.5–7.2 |
| Rhizobium sp. M-11 (FERM BP-4130) | 25,400 | About 45 | About 6.0–7.5 | Up to about 40 | About 5.0–10.0 |
| Arthrobacter sp. Q36 (FERM BP-4316) | 22,700 | About 45 | About 6.0–7.5 | Up to about 45 | About 5.0–10.0 |

In accordance with the method in Experiment 25, the experiment to prepare trehalose by the partially purified enzyme preparations from non-reducing saccharides, having a trehalose structure as an end unit and a glucose polymerization degree of 3 or more, was conducted. As a result, it was revealed that similarly as the trehalose-releasing enzyme from *Rhizobium sp.* M-11, all the preparations release trehalose from α-glycosyltrehalose.

EXPERIMENT 27
Influence of starch liquefaction decree and enzyme for preparing high trehalose content saccharide composition To prepare high trehalose content saccharide compositions from starch, the influence of the combination of enzymes and the liquefaction degrees of starch were studied. A 20% corn starch suspension was mixed with 0.1% calcium carbonate, d.s.b., and the mixture was adjusted to pH 6.5, mixed with 0.1–2.0% per g starch, d.s.b., of "TERMAMYL", α-amylase commercialized by Novo Industri A/S, Copenhagen, Denmark, enzymatically reacted at 95° C. for 15 min, and autoclaved at 120° C. for 10 min into a liquefied solution (DE 2.5–20.5). The resultant mixture was promptly cooled, and then mixed with 5 units/g starch, d.s.b., of a purified non-reducing saccharide-forming enzyme prepared by the method in Experiment 2, 10 units/g starch, d.s.b., of a purified trehalose-releasing enzyme prepared by the method in Experiment 15, 500 units/g starch, d.s.b., of a starch debranching isoamylase specimen commercialized by Hayashibara Biochemical Laboratories, Inc., Okayama, Japan, and 5 units/g starch, d.s.b., of a cyclomaltodextrin glucanotransferase specimen commercialized by Hayashibara Biochemical Laboratories, inc., Okayama, Japan, followed by the enzymatic reaction at pH 6.0 and 45° C. for 24 hours. The reaction mixture was heated at 95° C. for 10 min cooled, mixed with 10 units/g starch, d.s.b., of glucoamylase, and enzymatically reacted at pH 5.0 for 10 hours. The reaction mixture thus obtained was analyzed on HPLC and examined for trehalose content (w/w %, d.s.b.) with respect to the total carbohydrates. As a control, a liquefied starch solution was first subjected to the action of the non-reducing saccharide-forming enzyme and the trehalose-releasing enzyme, then the reaction mixture was similarly as above subjected to the action of glucoamylase, followed by examining the resultant mixture on HPLC. The results are in Table 19.

TABLE 19

| Percentage of α-amylase added to starch | DE | Combination of enzyme | | | |
|---|---|---|---|---|---|
| | | N + T | N + T + D | N + T + C | N + T + D + C |
| 0.1 | 2.5 | 21.3 | 79.6 | 76.2 | 84.3 |
| 0.4 | 4.8 | 22.5 | 69.7 | 67.7 | 76.9 |
| 0.6 | 7.8 | 23.3 | 63.2 | 59.1 | 68.2 |
| 1.0 | 12.5 | 23.7 | 56.0 | 51.3 | 62.5 |
| 1.2 | 14.8 | 25.3 | 50.3 | 44.7 | 58.4 |
| 1.5 | 17.3 | 22.4 | 44.2 | 39.2 | 48.3 |
| 2.0 | 20.5 | 18.6 | 38.4 | 34.9 | 46.1 |

Note : In the Table, the symbols "N", "T", "D" and "C" mean non-reducing saccharide-forming enzyme, trehalose-releasing enzyme, starch debranching enzyme, and cyclomaltodextrin glucanotransferase.

As is evident from the results in Table 19, it was revealed that in the case of preparing high trehalose content saccharide compositions from starch, a relatively-low liquefaction degree of starch, preferably, a DE less than 15, more preferably, a DE less than 10, is satisfactory. It was also found that, when the non-reducing saccharide-forming enzyme and the trehalose-releasing enzyme are used in combination with starch debranching enzyme and/or cyclomaltodextrin glucanotransferase, the trehalose yield from starch increases up to about 2–4 fold higher than that yielded by only using the former two enzymes. Therefore, the combination use is advantageous for an industrial-scale production of trehalose from starch.

The following Examples A and B illustrate the preparation of the present saccharide compositions with a reduced reducibility and compositions containing the same respectively:

EXAMPLE A-1

Potato starch was prepared into an about 20 w/v % suspension which was then mixed with 0.3 w/v % oxalic acid and autoclaved, cooled and neutralized with calcium carbonate to obtain a liquefied solution with a pH of 6.5 and a DE of about 12. To the solution was added 2 units/g starch, d.s.b., of a purified non-reducing saccharide-forming enzyme and 300 units/g starch, d.s.b., of isoamylase, and enzymatically reacted at 45° C. for 24 hours. The reaction mixture was heated to 95° C. to inactivate the remaining enzyme, cooled and filtered to obtain a supernatant which was then in usual manner decolored with an activated charcoal, desalted and purified with ion-exchangers in H—and OH-form, and concentrated to obtain an about 50% syrup in a yield of about 90%, d.s.b. The product, a saccharide composition with a reduced reducibility which had a DE of about 8 and contained α-glycosyltrehalose and reducing amylaceous saccharides, was placed in an autoclave, mixed with 10% Raney nickel, and heated up to a temperature of 90°–120° C. while stirring, followed by increasing the hydrogen pressure to 20–120 kg/cm² to terminate the hydrogenation. Thereafter, the Raney nickel was removed, and, in usual manner, decolored, desalted, purified and concentrated to obtain a 70% syrup in a yield of about 80%, d.s.b. The product, a saccharide composition with a reduced reducibility (DE of less than 1) which contains sugar alcohols and non-reducing saccharides having a trehalose structure, has a satisfactorily mild and high-quality sweetness, relatively-low viscosity, and adequate moisture-retaining ability, and can be arbitrarily used as a sweetener, taste-improving agent, quality-improving agent, stabilizer, filler, excipient and/or diluent in a variety of compositions such as foods, cosmetics and pharmaceuticals.

EXAMPLE A-2

Tapioca starch was prepared into an about 25% suspension which was then mixed with 0.2% per g starch, d.s.b., of "NEO-SPITASE", α-amylase commercialized by Nagase Biochemicals, Ltd., Kyoto, Japan. The resultant suspension was enzymatically reacted at 85°–90° C. for about 20 min, then autoclaved at 120° C. and promptly cooled to obtain a liquefied solution with a DE of about 4. To the solution were added 5 units/g starch, d.s.b., of a purified non-reducing saccharide-forming enzyme obtained by the method in Experiment 9, 100 units/g starch, d.s.b., of pullulanase commercialized by Hayashibara Biochemical Laboratories, Inc., Okayama, Japan, and 20 units/g starch, d.s.b., of maltotetraose-forming enzyme produced by Hayashibara Biochemical Laboratories, Inc., Okayama, Japan, and the mixture was enzymatically reacted at pH 6.5 and 40° C. for 36 hours. The reaction mixture was similarly as in Example A-1 heated to inactivate the remaining enzyme, purified and concentrated into an about 60% solution. To increase the content of non-reducing saccharides in the solution, it was column chromatographed with "XT-1016", a strong-acid cation exchange resin in Ca²⁺-form commercialized by Tokyo Organic Chemical Industries Ltd., Tokyo, Japan. The procedure was as follows: The resin was packed in 4 jacketed-stainless steel columns, having an inner diameter of 5.4 cm, which were then cascaded in series to give a total gel-bed depth of 20 m. The columns were heated to give the inner column temperature of 55° C., and fed with 5 v/v % of the solution as a feed solution while keeping at the temperature, followed by fractionating it by feeding to the columns with 55° C. hot water at SV 0.2 to collect fractions rich in non-reducing saccharides having a glucose polymerization degree of 4–6. The fractions thus obtained were pooled, purified and concentrated into an about 50% syrup, d.s.b. The syrup, a saccharide composition with a reduced reducibility and a DE 5.4 which contains α-glycosyltrehalose and reducing saccharides, was in accordance with the method in Example A-1 hydrogenated, purified and concentrated to obtain a 70% syrup in a yield of about 50%, d.s.b. The product, a saccharide composition with a reduced reducibility (DE of less than 1) which contains sugar alcohols and non-reducing saccharides having a trehalose structure within the molecules, has a satisfactorily mild and high-quality sweetness, relatively-low viscosity, and adequate moisture-retaining ability, and can be arbitrarily used as a sweetener, taste-improving agent, quality-improving agent, stabilizer, filler, excipient and/or diluent in a variety of compositions such as foods, cosmetics and pharmaceuticals.

EXAMPLE A-3

Corn starch was prepared into a 30% suspension which was then mixed with calcium carbonate to give the final concentration of 0.1%, d.s.b., and the resultant mixture was adjusted to pH 6.5, admixed with 0.3% per g starch, d.s.b., of "TERMAMYL 60L", α-amylase commercialized by Novo Industri A/S Copenhagen, Denmark, and subjected to an enzymatic reaction at 95° C. for 15 min. The reaction mixture was autoclaved at 120° C., promptly cooled into a liquefied solution (DE 4) which was then admixed with 4 units/g starch, d.s.b., of a purified non-reducing saccharide-forming enzyme obtained by the method in Experiment 2, 300 units/g starch, d.s.b., of isoamylase, and 5 units/g starch, d.s.b., of cyclomaltodextrin glucano-transferase commercialized by Hayashibara Biochemical Laboratories, Inc., Okayama, Japan, and subjected to an enzymatic reaction at pH 6.3 and 45° C. for 48 hours. The reaction mixture was heated at 95° C. for 10 min, cooled, admixed with 10 units/g starch, d.s.b., of β-amylase, and enzymatically reacted at 55° C. and pH 5.5 for 16 hours. The reaction mixture was heated to inactivate the remaining enzyme, and, in usual manner, decolored, desalted, purified and concentrated into an about 50% syrup. The syrup, a saccharide composition with a reduced reducibility which contained reducing saccharides and non-reducing saccharides such as those having a trehalose structure as an end unit and α-glycosyl α-glucosides, was in accordance with the method in Example A-1 hydrogenated, purified and concentrated to obtain a 70% syrup in a yield of about 80%, d.s.b. The product, a saccharide composition with a reduced reducibility (DE of less than 1) which contains sugar alcohols and non-reducing saccharides having a trehalose structure within the molecules, has a satisfactorily mild and high-quality sweetness, relatively-low viscosity, and adequate moisture-retaining ability, and can be arbitrarily used as a sweetener, taste-improving agent, quality-improving agent, stabilizer, filler, excipient and/or diluent in a variety of compositions such as foods, cosmetics and pharmaceuticals.

EXAMPLE A-4

A syrup obtained by the method in Example A-3 was prepared into an about 55% solution which was then column chromatographed with a strong-acid cation exchange resin in alkaline form in accordance with the method in Example A-2, followed by collecting fractions rich in non-reducing saccharides with a glucose polymerization degree of 3–6. The fractions were pooled, purified and concentrated into an about 50% syrup. The syrup, a saccharide composition (DE 8) with a reduced reducibility which contained reducing amylaceous saccharides and non-reducing saccharides such as α-glycosyl α-glucosides and those having a trehalose structure as an end unit, was in accordance with the method in Example A-1 hydrogenated, purified and concentrated to obtain a 70% syrup in a yield of about 30%, d.s.b. The syrup thus obtained is a saccharide composition with a reduced reducibility (DE of less than 1) which contains sugar alcohols and non-reducing saccharides having a trehalose structure within the molecules, and has a satisfactorily mild and high-quality sweetness, relatively-low viscosity, and adequate moisture-retaining ability. Thus, it can be arbitrarily used as a sweetener, taste-improving agent, quality-improving agent, stabilizer, filler, excipient and/or diluent in a variety of compositions such as foods, cosmetics and pharmaceuticals.

EXAMPLE A-5

Corn starch was prepared into an about 30% suspension, and, in accordance with the method in Example A-3, α-amylase was allowed to act on the suspension to obtain a liquefied solution (DE 4) which was then admixed with 5 units/g starch, d.s.b., of a purified non-reducing saccharide-forming enzyme obtained by the method in Experiment 2, 10 units/g starch, d.s.b., of a purified trehalose-releasing enzyme obtained by the method in Experiment 15, and 500 units/g starch, d.s.b., of isoamylase, and subjected to an enzymatic reaction at pH 6.0 and 40° C. for 48 hours. The reaction mixture containing 76.3% trehalose, d.s.b., was heated to inactivate the remaining enzyme, and, in usual manner, decolored, desalted, purified and concentrated into an about 45% syrup. The syrup thus obtained was a non-reducing saccharide composition rich in trehalose, and, in accordance with the method in Example A-1, it was hydrogenated, purified and concentrated into an about 85% solution. The resultant solution was placed in a crystallizer, crystallized while gently stirring and gradually cooling, transferred to a plastic plain vessel, allowed to stand at ambient temperature for 2 days, and aged to terminate the crystallization and to form a block. The resultant block was pulverized by a cutter to obtain a powdery saccharide composition with a reduced reducibility containing hydrous trehalose and sugar alcohols in a yield of 80% with respect to the material starch, d.s.b. The product with a reduced reducibility (DE of less than 1) is readily handleable and can be arbitrarily used as a sweetener, taste-improving agent, quality-improving agent, stabilizer, filler, excipient and/or diluent in a variety of compositions such as foods, cosmetics and pharmaceuticals.

EXAMPLE A-6

Tapioca starch was prepared into an about 30% suspension, and, in accordance with the method in Example A-2, α-amylase was allowed to act on the suspension to form a liquefied solution (DE 5), followed by adding to the solution 3 units/g starch, d.s.b., of a purified non-reducing saccharide-forming enzyme obtained by the method in Experiment 10, 5 units/g starch, d.s.b., of a purified trehalose-releasing enzyme obtained by the method in Experiment 23, and 200 units/g starch, d.s.b., of cyclomaltodextrin glucanotransferase, and subjecting the resultant mixture to an enzymatic reaction at 45° C. for 48 hours. The reaction mixture containing 84.7% trehalose was heated to inactivate the remaining enzyme, and, in usual manner, decolored, desalted, purified and continuously crystallized while concentrating. The resultant massecuite was separated by a basket-type centrifuge, and the resultant crystal was washed by spraying thereto a small amount of water to obtain a crystalline trehalose hydrate in a yield of about 55%, d.s.b. The resultant mother liquor, containing relatively-large amounts of reducing amylaceous saccharides, trehalose and non-reducing saccharide having a trehalose structure, was concentrated into a 50% syrup of saccharides with a reduced reducibility. In accordance with the method in Example A-1, the syrup was hydrogenated, purified and concentrated to obtain a 70% syrup in a yield of about 30%, d.s.b. The product, a saccharide composition with a reduced reducibility (DE of less than 1) which contains trehalose, sugar alcohols and non-reducing saccharides having a trehalose structure, has a mild and high-quality sweetness, relatively-low viscosity, and satisfactory moisture-retaining ability. Thus, it can be arbitrarily used as a sweetener, taste-improving agent, quality-improving agent, stability, filler, excipient and/or diluent in a variety of compositions.

EXAMPLE A-7

The heat inactivated reaction mixture in Example A-6 was mixed with 10 units/g substrate, d.s.b., of glucoamylase, and subjected to an enzymatic reaction at pH 5.0 and 50° C. for 10 hours. The resultant reaction mixture was heated to inactivate the remaining enzyme, and, in usual manner, decolored, desalted, purified and concentrated into a 45% syrup with a high trehalose content and a reduced reducibility. In accordance with the method in Example A-1, the syrup was hydrogenated and purified into an about 70% solution which was then placed in a crystallizer and crystallized while stirring and gradually cooling to obtain a massecuite with a crystallization percentage of about 40%. The massecuite was sprayed at a pressure of 150 kg/cm² from a nozzle mounted on the top of a drying tower while 85° C. hot air was blowing to the contents from the upper part of the drying tower and collecting the resultant crystalline powders on a wire netting conveyer provided in the basement of the drying tower. The crystalline powders were gradually transferred out of the drying tower and recovered while 45° C. hot air was blowing to the powders through under the conveyer. The crystalline powders thus obtained were placed in an aging tower and aged for 10 hours while a hot air was blowing to the contents to terminate the crystallization and drying. Thus, a saccharide powder with a reduced reducibility, which contained hydrous trehalose crystal and sorbitol, was obtained in a yield of about 75% with respect to the material starch, d.s.b. The powder with a reduced reducibility (DE of less than 1) is readily handleable and can be arbitrarily used as a sweetener, taste-improving agent, quality-improving agent, stabilizer, filler, excipient and/or diluent in a variety of compositions such as foods, cosmetics and pharmaceuticals.

EXAMPLE A-8

A mutant of *Rhizobium sp.* M-11 (FERM BP-4130) was inoculated in a nutrient culture medium and cultured in a fermenter for about 70 hours in accordance with the method in Experiment 1. The resultant culture was filtered with an SF membrane to remove cells to obtain an about 100 L supernatant which was then concentrated with a UF membrane into an about 5 L enzyme concentrate containing about 410 units/ml of a non-reducing saccharide-forming enzyme and about 490 units/ml of a trehalose-releasing enzyme. Corn starch was prepared into an about 33% suspension which was then treated with α-amylase to obtain a liquefied solution (DE of about 4) in accordance with the method in Example A-3, mixed with 0.02 ml per g starch, d.s.b., of the concentrated enzyme solution, 500 units/g starch, d.s.b., of isoamylase, and 5 units/g starch, d.s.b., of cyclomaltodextrin glucanotransferase, and enzymatically reacted at pH 6.2 and 40° C. for 48 hours. The reaction mixture was heated to inactivate the remaining enzyme, mixed with 10 units/g substrate, d.s.b., of glucoamylase, and enzymatically reacted at pH 5.0 and 50° C. for 10 hours. The resultant mixture containing 85.6% trehalose, d.s.b., was heated to inactivate the remaining enzyme, and, in usual manner, decolored, desalted, purified and concentrated to obtain a 45% syrup of saccharides rich in trehalose with a reduced reducibility. In accordance with the method in Example A-1, the syrup was hydrogenated, purified, and, in accordance with the method in Example A-5, concentrated and crystallized to form a block which was then pulverized with a cutter to obtain a saccharide powder with a reduced reducibility, which contains hydrous trehalose crystal and sorbitol, in a yield of about 80% with respect to the material starch, d.s.b. The product with a reduced reducibility (DE of less than 1) is readily handleable and can be used in a variety of compositions such as foods, cosmetics and pharmaceuticals.

EXAMPLE A-9

Into a fermenter was poured a liquid nutrient culture medium consisting of 2 w/v % glucose, 0.5 w/v % polypeptone, 0.1 w/v % yeast extract, 0.1 w/v % dipotassium phosphate, 0.06 w/v % sodium dihydrogen phosphate, 0.05 w/v % magnesium sulfate, 0.5 w/v % calcium carbonate, and water, and the medium was sterilized by heating, cooled and inoculated with a seed culture of Pimelobacter sp. R48 (FERM BP-4315), followed by the incubation at 27° C. for about 40 hours under stirring conditions. The resultant culture had 0.55 units/ml of a maltose-trehalose converting enzyme. 0.18 kg of wet cells collected from 18 L of the culture was suspended in 10 mM phosphate buffer (pH 7.0), and about 1.5 L of the suspension was treated with an ultrasonic cell disrupter to disrupt cells. The resultant mixture was centrifuged to obtain a supernatant which was then concentrated with a UF membrane to obtain an about 500 ml of a concentrated enzyme solution containing about 18 units/ml of a maltose-trehalose converting enzyme. To 15% corn starch suspension (pH 5.5) was added 2 units/g starch, d.s.b., of "SPITASE HS", α-amylase commercialized by Nagase Biochemicals, Ltd., Kyoto, Japan, and the mixture was stirred, heated to effect gelatinization and liquefaction, and then promptly autoclaved at 120° C. for 20 min. Thereafter, the resultant mixture was cooled to 55° C., adjusted to pH 5.0, mixed with 300 units/g starch, d.s.b., of isoamylase, 20 units/g starch, d.s.b., of β-amylase commercialized by Nagase Biochemicals, Ltd., Kyoto, Japan, and enzymatically reacted for 24 hours to obtain an about 92% maltose solution. The solution thus obtained was heated at 100° C. for 20 min, cooled to 20° C., adjusted to pH 7.0, and mixed with 1.5 units/g starch, d.s.b., of the concentrated enzyme solution prepared in the above, and enzymatically reacted for 72 hours. The resultant reaction mixture was heated at 95° C. for 10 min, cooled, and, in usual manner, decolored with an activated charcoal, filtered, desalted and purified with ion-exchangers in H— and OH-form, and concentrated into an about 50% syrup.

The product contained about 64% trehalose, d.s.b., and had a low DE of 18.0. In accordance with the method in Example A-1, the syrup was hydrogenated, purified and concentrated to obtain an about 70% syrup in a yield of about 80%, d.s.b. The product, a saccharide syrup with a reduced reducibility (DE of less than 1) which contains trehalose, maltitol and a small amount of sorbitol, has a mild sweetness, adequate viscosity, and satisfactory moisture retaining ability, and these render it arbitrarily useful in a variety of compositions such as foods, cosmetics and pharmaceuticals.

EXAMPLE B-1

Sweetener

One part by weight of a powdery saccharide composition with a reduced reducibility, obtained by the method in Example A-7, was homogeneously mixed with 0.01 part by weight of "αG SWEET", α-glycosyl stevioside commercialized by Toyo Sugar Refining Co., Ltd., Tokyo, Japan, and 0.01 part by weight of L-aspartyl-L-phenylalanine methylester commercialized by Ajinomoto Co., Ltd., Tokyo, Japan, and the mixture was fed to a granulator into a granular sweetener. The product has a satisfactory sweetness, about 2-fold higher sweetening power of sucrose, and an about half caloric value of sucrose. The product with a satisfactory stability does not affect and decompose other sweeteners with a relatively-high sweetness even when mixed with them, and because of this it can be suitably used as a low-caloric sweetener for low-caloric food products for fat persons and diabetics who restrict their calorie intake. From the product are scarcely formed acids and insoluble glucans when dental carries-inducing microorganisms act on it, and this renders it useful for sweetening food products directed to the prevention of dental carries.

EXAMPLE B-2

Hard candy

One hundred parts by weight of 55% sucrose solution was mixed while heating with 30 parts by weight of a syrup containing a saccharide composition with a reduced reducibility obtained by the method in Example A-1, and the resultant mixture was concentrated by heating in vacuo until the moisture content lowered to below 2%. The concentrate was admixed with one part by weight of citric acid and adequate amounts of a lemon flavor and a coloring agent, and the resultant mixture was formed in usual manner into the desired product. The product is a high-quality hard candy which has a satisfactory taste and biting property but has no fear of changing the shape and causing the crystallization of sucrose.

EXAMPLE B-3

Chocolate

Forty parts by weight of cacao paste, 10 parts by weight of cacao butter, 30 parts by weight of sucrose, and 20 parts by weight of a powdery saccharide composition with a reduced reducibility obtained by the method in Example A-8 were mixed, and the mixture was passed through a refiner to reduce the particle size of the contents, fed to a conche and kneaded at 50° C. for 2 days. Before completion of the kneading, 0.5 parts by weight of lecithin was added to and homogeneously mixed with the resultant. The mixture thus obtained was adjusted to 31° C. with a thermoregulator, poured into a mold before the butter was solidified, deaerated with a vibrator, and passed through a cooling tunnel at 10° C. for 20 min to solidify the contents. The contents were removed from the mold and packed to obtain the desired product. The product has a satisfactory color, gloss, texture, smooth meltability in the mouth, mild sweetness, and high-quality flavor without substantially exhibiting hygroscopicity.

EXAMPLE B-4

Chewing gum

Three parts by weight of gum base was melted by heating until it softened, and which was then mixed with 4 parts by weight of sucrose and 3 parts by weight of a powdery saccharide composition with a reduced reducibility obtained by the method in Example A-5, and further mixed with adequate amounts of a flavor and a coloring agent. The resultant mixture was in usual manner kneaded by a roll, formed and packed to obtain the desired product. The product is a chewing gum having a satisfactory texture and taste.

EXAMPLE B-5

Sweetened condensed milk

Three parts by weight of a syrupy saccharide composition with a reduced reducibility obtained by the method in Example A-3 and one part by weight of sucrose were dissolved in 100 parts by weight of fresh milk, and the resultant solution was sterilized by heating on a plate heater, and condensed into a 70% solution, followed by aseptically canning the solution into the desired product. The product with a mild sweetness and a satisfactory taste can be arbitrarily used as a seasoning for baby foods, fruit, coffee, cocoa and tea.

EXAMPLE B-6
Beverage containing lactic acid bacteria

One hundred and seventy-five parts by weight of defatted milk, 80 parts by weight of a powdery saccharide composition with a reduced reducibility prepared by the method in Example A-5, and 50 parts by weight of a high lactosucrose content powder disclosed in Japanese Patent Laid-Open No.281,795/92 were dissolved in 1,200 parts by weight of water, and the resultant solution was sterilized by heating at 65° C. for 30 min, cooled to 40° C., admixed in usual manner with 30 parts by weight of lactic acid bacteria as a starter, and incubated at 37° C. for 8 hours to obtain a beverage containing lactic acid bacteria. The product is a beverage which contains lactic acid bacteria and has a satisfactory taste and flavor. The product containing oligosaccharides stably keeps lactic acid bacteria and promotes the growth of bifid bacteria.

EXAMPLE B-7
Powdered juice

Thirty-three parts by weight of a powdered orange juice prepared by spray drying was mixed to homogeneity under stirring conditions with 50 parts by weight of a powdery saccharide composition with a reduced reducibility obtained by the method in Example A-5, 10 parts by weight of sucrose, 0.65 parts by weight of anhydrous citric acid, 0.1 part by weight of malic acid, 0.1 part by weight of L-ascorbic acid, 0.1 part by weight of sodium citrate, 0.5 parts by weight of pullulan, and an adequate amount of a powdered flavor. The resultant mixture was pulverized, fed to a fluidized-bed granulator and granulated for 30 min by spraying to the contents a high trehalose content syrup, as a binder, obtained by the method in Example A-6 while 40° C. air was sending to the contents. The granules thus obtained were weighed and packed to obtain the desired product. The product, a powdered juice containing about 30% orange juice, d.s.b., was stable for a relatively-long period of time without giving an unsatisfactory smell and taste.

EXAMPLE B-8
Custard cream

One hundred parts by weight of corn starch, 100 parts by weight of a syrupy saccharide composition obtained by the method in Example A-6, 80 parts by weight of maltose, 20 parts by weight of sucrose, and one part by weight of salt were mixed to homogeneity. The mixture was admixed with 280 parts by weight of egg, and gradually mixed with 1,000 parts by weight of a boiling milk. The resultant mixture was continued stirring while heating, and the heating was stopped when the corn starch in the mixture was completely gelatinized to give the whole contents semitransparent, followed by cooling the resultant and adding thereto an adequate amount of a vanilla flavor. The resultant mixture was weighed, injected and packed to obtain the desired product. The product has a smooth surface and gloss, as well as a mild taste and sweetness.

EXAMPLE B-9
"Uiro-no-moto" (premix of sweet rice jelly)

Ninety parts by weight of rice powder was mixed to homogeneity with 20 parts by weight of corn starch, 40 parts by weight of sucrose, 80 parts by weight of a powdery saccharide composition with a reduced reducibility obtained by the method in Example A-5, 4 parts by weight of pullulan to obtain a "uiro-no-moto". The product was mixed with adequate amounts of water and a "matcha" (powdered tea), and the mixture was placed in a container and steamed up for 60 hours to obtain a "matcha uiro". The product has a satisfactory gloss, biting property and flavor, and it has a relatively-long shelf-life because the retrogradation of starch therein is well inhibited.

EXAMPLE B-10
"An" (beans paste)

To 10 parts by weight of "adzuki" beans as a material was in usual manner added water and boiled, followed by removing water-soluble impurities and the astringency and harshness of the beans to obtain about 21 kg "adzuki-tsubu-an". To the resultant was added 14 parts by weight of sucrose, 5 parts by weight of a syrupy saccharide composition obtained by the method in Example A-9, and 4 parts by weight of water, and the resultant mixture was successively boiled, mixed with a small amount of salad oil, and carefully kneaded up so as not to jam the beans, followed by yielding about 35 kg of the desired product. The product is free from discoloration inducible by boiling and has a satisfactory taste, flavor and biting property, and these render it useful as a material "an" for bean-jam buns, buns with bean-jam filling, dumplings, bean-jam-filled wafers, sherbets and ice creams.

EXAMPLE B-11
Bread

One hundred parts by weight of wheat flour, 2 parts by weight of yeast, 5 parts by weight of sugar, one part by weight of a powdery saccharide composition with a reduced reducibility obtained by the method in Example A-7, 0.1 part by weight of inorganic yeast food were kneaded with water in usual manner, and the mixture was successively fermented at 26° C. for 2 hours, aged for 30 min and baked up the resultant. The product is a high-quality bread having a satisfactory hue and rising, as well as a satisfactory elasticity and mild sweetness.

EXAMPLE B-12
Ham

To one thousand parts by weight of ham meat slices were added and ground to homogeneity 15 parts by weight of salt and 3 parts by weight of potassium nitrate, and the resultant slices were piled up and allowed to stand overnight in a cold-storage room. Thereafter, the resultant slices were first soaked for 7 days in a cold-storage room in a salt solution consisting of 500 parts by weight of water, 100 parts by weight of salt, 3 parts by weight potassium nitrate, 40 parts by weight of a powdery saccharide composition with a reduced reducibility prepared by the method in Example A-8, and an adequate amount of a spice, then washed with cold water in usual manner, tied up, smoked, cooked, cooled and packed to obtain the desired product. The product is a high-quality ham having a satisfactory hue, taste and flavor.

EXAMPLE B-13
Powdery peptide

One part by weight of a 40% solution of "HINUTE S", a peptide solution of edible soy beans commercialized by Fuji Oil Co., Ltd., Tokyo, Japan, was mixed with 2 parts by weight of a powdery saccharide composition prepared by the method in Example A-8, and the resultant mixture was placed in a plastic vessel, dried in vacuo at 50° C., and pulverized to obtain a powdery peptide. The product having a satisfactory taste and flavor can be arbitrarily used as a material for confectioneries such as premixes, sherbets and ice creams, as well as baby foods and therapeutic nutrition in the form of an oral or intubation feeding.

EXAMPLE B-14

Cosmetic cream

Two parts by weight of polyoxyethylene glycol monostearate, 5 parts by weight of glyceryl monostearate, self-emulsifying, 2 parts by weight of a powdery saccharide composition obtained by the method in Example A-5, one part by weight of α-glycosyl rutin, one part by weight of liquid petrolatum, 10 parts by weight of glyceryl tri-2-ethylhexanoate, and an adequate amount of an antiseptic were dissolved by heating in usual manner. The resultant solution was mixed with 2 parts by weight of L-lactic acid, 5 parts by weight of 1,3-butylene glycol and 66 parts by weight of refined water, and the resultant mixture was emulsified by a homogenizer and admixed with an adequate amount of a flavor while stirring to obtain a cosmetic cream. The product exhibits an antioxidant activity and has a relatively-high stability, and these render it arbitrarily useful as a high-quality sunscreen, skin-refining agent or skin-whitening agent.

EXAMPLE B-15

Solid pharmaceutical

To a column of an immobilized anti-human interferon-α antibody was fed in usual manner a natural human interferon-α preparation, produced by Hayashibara Biochemical Laboratories, Inc. Okayama, Japan, to adsorb the interferon-α on the antibody, and fed with a buffer containing calf serum albumin as a stabilizer, followed by removing an excessive amount of the albumin. Thereafter, the interferon-α was eluted from the column with a physiological saline containing 5 w/v % of a powdery saccharide composition with a reduced reducibility, obtained by the method in Example A-7, while varying the pH of the physiological saline. The resultant eluate was membrane filtered, and the filtrate was dehydrated by the addition of about 20-fold volumes of "FINETOSE®", an anhydrous crystalline maltose powder commercialized by Hayashibara Shoji Inc., Okayama, Japan, followed by pulverizing the resultant dehydrated product, and tabletting the resultant by a tabletting machine into tablets containing about 150 units of the natural human interferon-α per one tablet, 200 mg weight. The product can be orally administered as a sublingual tablet to patients at a dose of 1–10 tablets/adult/day, and arbitrarily used to treat viral diseases, allergys, rheumatisms, diabetes and malignant tumors. More particularly, the product can be suitably used as a therapeutic agent for AIDS and hepatitis, the number of patients of which has been remarkably increasing. The present non-reducing saccharides and anhydrous crystalline maltose incorporated in the product act as a stabilizer for the natural human interferon-α, so that the activity is well retained for a relatively-long period of time even when allowed to stand at ambient temperature.

EXAMPLE B-16

Sugar coated tablet

A crude tablet as a core, 150 mg weight, was coated with a solution consisting of 40 parts by weight of a powdery saccharide composition obtained by the method in Example A-8, 2 parts by weight of pullulan having an average molecular weight of 200,000, 30 parts by weight of water, 25 parts by weight of talc, and 3 parts by weight of titanium oxide until the total weight reached to about 230 mg, and the resultant was further coated with a solution consisting of 65 parts by weight of a fresh preparation of the same powdery saccharide composition, one part by weight of pullulan, and 34 parts by weight of water, and glossed with a liquid wax to obtain a sugar coated tablet having a satisfactory gloss and appearance. The product has a relatively-high shock tolerance and retains its high quality for a relatively-long period of time.

EXAMPLE B-17

Toothpaste

A toothpaste was obtained by mixing the materials as indicated below in usual manner. Because the product has an adequate sweetness, it can be advantageously used for children.

| Composition | |
|---|---|
| Calcium secondary phosphate | 45.0% |
| Pullulan | 2.95% |
| Sodium lauryl sulfate | 1.5% |
| Glycerine | 20.0% |
| Polyoxyethylene sorbitan laurate | 0.5% |
| Antiseptic | 0.05% |
| Saccharide composition with a reduced reducibility obtained by the method in Example A-5 | 12.0% |
| Maltitol | 5.0% |
| Water | 13.0% |

EXAMPLE B-18

Solid preparation for intubation feeding

A composition, which consists of 500 parts by weight of a powdery saccharide composition with a reduced reducibility obtained by the method in Example A-7, 270 parts by weight of powdered egg yolk, 209 parts by weight of defatted milk, 4.4 parts by weight of sodium chloride, 1.8 parts by weight of potassium chloride, 4 parts by weight of magnesium sulfate, 0.01 part by weight of thiamine, 0.1 part by weight of sodium ascorbate, 0.6 parts by weight of vitamin E acetate, and 0.04 parts by weight of nicotinic acid amide, was prepared. Twenty-five aliquots of the composition were injected into laminated small bags and heat-sealed to obtain the desired product. In use, one bag of the product is dissolved in about 150–300 ml water into an intubation feeding which is then administered by the oral- or intubation-method to the nasal cavity, stomach or intestines, and effectively utilized by the body as an energy-supplementing agent.

EXAMPLE B-19

Ointment for treating trauma

Two hundred parts by weight of a powdery saccharide composition with a reduced reducibility, obtained by the method in Example A-5, and 300 parts by weight of maltose were mixed with 3 parts by weight of iodine dissolved in 50 parts by weight of methanol, and the resultant solution was admixed with 200 parts by weight of 10 w/v % pullulan solution to obtain the desired product with an adequate spreadability and adhesiveness. The product exerts a bactericidal activity due to the iodine and acts as an energy-supplementing agent for living cells due to the trehalose, and therefore, it can shorten the healing period and readily cure the wounded sites. [Effect on the Invention]

As is evident from above, the present saccharide composition, which comprises sugar alcohols and non-reducing saccharides consisting of trehalose and/or saccharides having a trehalose structure, has a satisfactory stability and a high-quality sweetness. The saccharide composition is assimilated, absorbed and utilized by the body when orally administered. More particularly, the trehalose contained in the saccharide composition is readily metabolized and utilized by the body. Thus, the present saccharide composition can be arbitrarily used as a sweetener, taste-improving agent, quality-improving agent, stabilizer, filler, excipient and diluent in a variety of compositions such as foods, cosmetics and pharmaceuticals. The reducing saccharides with a reduced reducibility used as a material for the present saccharide composition include (i) those prepared by allowing a non-reducing saccharide-forming enzyme together with a starch debranching enzyme and/or cyclomaltodextrin glucanotransferase to act on a liquefied starch solution whereby non-reducing saccharides such as trehalose and saccharides having a trehalose structure are formed in an increased yield to obtain the objective saccharide composition with a reduced reducibility and a relatively-low molecular weight and viscosity, and (ii) those prepared by allowing a maltose-trehalose converting enzyme to act on maltose to form a saccharide composition of maltose and trehalose. These saccharide compositions are satisfactorily used as a material for the present invention and facilitate the industrial-scale preparation of the present invention.

The establishment of the present invention provides a novel technique for preparing non-reducing saccharides in an industrial scale and at a relatively-low cost, which has been in great demand and far from being readily produced from starch as a cheap and abundant material, i.e., saccharide compositions with a reduced reducibility, and gives a great contribution to the fields such as food-, cosmetic- and pharmaceutical-industries as well as forestry, fisheries, and agricultural-, livestock- and chemical-industries. Thus, the industrial significance of the present invention is unfathomable.

While the invention has been particularly shown and described with reference to preferred embodiments thereof, it will be understood by those skilled in the art that the foregoing and other changes in form and details can be made therein without departing from the spirit and scope of the invention.

What is claimed in:

1. A process for preparing a saccharide composition with a reduced reducibility, which comprises:
   hydrogenating a saccharide mixture comprising a reducing amylaceous saccharide and a non-reducing saccharide selected from the group consisting of trehalose, a saccharide having a trehalose structure within the molecule, a saccharide having a trehalose structure as an end unit, and mixtures thereof; and
   collecting the resultant mixture comprising said non-reducing saccharide and a formed sugar alcohol.

2. The process as claimed in claim 1, wherein said saccharide mixture is obtainable by allowing a non-reducing saccharide-forming enzyme together with or without a trehalose-releasing enzyme to act on a reducing partial starch hydrolysate.

3. The process as claimed in claim 1, wherein said reducing amylaceous saccharide is one or more members selected from the group consisting of glucose, maltose, maltotriose, maltotetraose and maltopentaose.

4. The process as claimed in claim 1, wherein said saccharide mixture is obtainable by allowing a maltose-trehalose converting enzyme to act on a reducing partial starch hydrolysate containing maltose.

5. The process as claimed in claim 1, wherein said saccharide composition has a dextrose equivalent (DE) of less than 1.

6. A process for preparing a saccharide composition with a reduced reducibility, which comprises:
   either allowing a non-reducing saccharide-forming enzyme together with a starch debranching enzyme and/or cyclomaltodextrin glucanotransferase, or allowing a non-reducing saccharide-forming enzyme and a trehalose-releasing enzyme together with a starch debranching enzyme and/or cyclomaltodextrin glucanotransferase to act on a liquified starch solution;
   hydrogenating the resultant saccharide mixture with a reduced reducibility containing a reducing amylaceous saccharide and a non-reducing saccharide selected from the group consisting of trehalose, a saccharide having a trehalose structure within the molecule, a saccharide having a trehalose structure as an end unit, and mixtures thereof; and
   collecting the resultant saccharide composition comprising said non-reducing saccharide and a formed sugar alcohol.

7. The process as claimed in claim 6, wherein said liquefied starch solution is obtainable by liquefying a starch suspension with a concentration of 10 w/w % or more to give a dextrose equivalent (DE) of less than 15.

8. The process as claimed in claim 6, wherein said saccharide composition has a dextrose equivalent (DE) of less than 1.

9. A method for reducing the reducibility of a saccharide mixture with a reduced reducibility which comprises a reducing amylaceous saccharide and a non-reducing saccharide selected from the group consisting of trehalose, a saccharide having a trehalose structure within the molecule, a saccharide having a trehalose structure as an end unit, and mixtures thereof, which contains a step of hydrogenating said saccharide mixture to form a saccharide composition comprising said non-reducing saccharide and a formed sugar alcohol.

* * * * *